(12) United States Patent
Hakoshima

(10) Patent No.: US 10,722,113 B2
(45) Date of Patent: Jul. 28, 2020

(54) GAZE DETECTION APPARATUS AND GAZE DETECTION METHOD

(71) Applicant: JVC KENWOOD Corporation, Yokohama-shi, Kanagawa (JP)

(72) Inventor: Shuji Hakoshima, Yokohama (JP)

(73) Assignee: JVC KENWOOD Corporation, Yokohama-Shi (JP)

( * ) Notice: Subject to any disclaimer, the term of this patent is extended or adjusted under 35 U.S.C. 154(b) by 227 days.

(21) Appl. No.: 15/960,617

(22) Filed: Apr. 24, 2018

(65) Prior Publication Data

US 2018/0235466 A1    Aug. 23, 2018

Related U.S. Application Data

(63) Continuation of application No. PCT/JP2016/079357, filed on Oct. 3, 2016.

(30) Foreign Application Priority Data

Dec. 1, 2015   (JP) ................. 2015-235180

(51) Int. Cl.
*A61B 3/113*    (2006.01)
*G06F 3/01*    (2006.01)
(Continued)

(52) U.S. Cl.
CPC ............ *A61B 3/113* (2013.01); *A61B 3/107* (2013.01); *G02B 27/0093* (2013.01);
(Continued)

(58) Field of Classification Search
CPC ........... A61B 3/08; A61B 3/085; A61B 3/107; A61B 3/113; G02B 27/0093
(Continued)

(56) References Cited

U.S. PATENT DOCUMENTS 5,889,577 A * 3/1999 Kohayakawa ......... A61B 3/024
351/208
7,533,989 B2 * 5/2009 Ebisawa ................ A61B 3/113
351/208
(Continued)

FOREIGN PATENT DOCUMENTS

JP        2739331      1/1998
WO   WO-2011021936 A1 * 2/2011 ............. A61B 3/113
(Continued)

OTHER PUBLICATIONS

International Search Report and Written Opinion for International Patent Application No. PCT/JP2016/079357 dated Dec. 20, 2016, 9 pages.
(Continued)

*Primary Examiner* — Nicholas R. Pasko
(74) *Attorney, Agent, or Firm* — Amin, Turocy & Watson, LLP

(57) ABSTRACT

A gaze detection apparatus includes a light source configured to irradiate an eyeball of a subject with detection light, a position detection unit configured to detect positions of pupil centers indicating centers of pupils of right and left respective eyeballs and positions of corneal reflection centers indicating centers of corneal reflexes of the right and left respective eyeballs from an image of the eyeball irradiated with the detection light, a curvature radius calculation unit configured to calculate corneal curvature radii of the right and left respective eyeballs from a position of the light source and the positions of the corneal reflection centers, a gaze detection unit configured to detect gaze directions of the right and left respective eyeballs from the positions of the pupil centers and the corneal curvature radii, a viewpoint detection unit, an output control unit, and a determination unit.

8 Claims, 22 Drawing Sheets

(51) Int. Cl.
  *G02B 27/00* (2006.01)
  *A61B 3/107* (2006.01)
  *A61B 3/08* (2006.01)
  *A61B 3/00* (2006.01)
(52) U.S. Cl.
  CPC ............ *G06F 3/013* (2013.01); *A61B 3/0008* (2013.01); *A61B 3/0025* (2013.01); *A61B 3/0041* (2013.01); *A61B 3/085* (2013.01)
(58) Field of Classification Search
  USPC .................................................. 351/209, 212
  See application file for complete search history.

(56) References Cited

U.S. PATENT DOCUMENTS

| | | | | |
|---|---|---|---|---|
| 7,878,652 | B2* | 2/2011 | Chen | A61B 3/0008 351/205 |
| 8,403,480 | B2* | 3/2013 | Chen | A61B 3/08 351/200 |
| 8,820,930 | B2* | 9/2014 | Fateh | A61H 5/00 351/205 |
| 2004/0015098 | A1* | 1/2004 | Souvestre | A61B 3/113 600/558 |
| 2015/0190050 | A1* | 7/2015 | Samadani | A61B 5/7264 600/558 |
| 2015/0199812 | A1* | 7/2015 | Hakoshima | A61B 3/113 348/78 |
| 2015/0257967 | A1* | 9/2015 | Simmons | A61B 5/168 351/202 |
| 2015/0265146 | A1* | 9/2015 | Bloom | A61B 3/085 351/202 |
| 2015/0374223 | A1* | 12/2015 | Shudo | A61B 5/163 351/210 |
| 2016/0150956 | A1 | 6/2016 | Hakoshima et al. | |
| 2016/0262613 | A1* | 9/2016 | Klin | A61B 5/167 |
| 2017/0007119 | A1* | 1/2017 | Cornsweet | A61B 5/4064 |
| 2017/0007120 | A1 | 1/2017 | Shudo | |
| 2018/0168444 | A1* | 6/2018 | Foss | A61B 3/024 |
| 2018/0239427 | A1* | 8/2018 | Hakoshima | G06F 3/013 |

FOREIGN PATENT DOCUMENTS

| | | | | |
|---|---|---|---|---|
| WO | WO-2014051010 | A1* | 4/2014 | ............ H04N 7/18 |
| WO | WO-2014136803 | A1* | 9/2014 | ............ A61B 5/168 |
| WO | 2014/204904 | | 12/2014 | |
| WO | 2015/146491 | | 10/2015 | |

OTHER PUBLICATIONS

Extended European Search Report for European Patent Application No. 16870283.5 dated Nov. 22, 2018.

* cited by examiner

GAZE DETECTION APPARATUS AND GAZE DETECTION METHOD

CROSS-REFERENCE TO RELATED APPLICATION(S)

This application is a continuation of PCT international application Ser. No. PCT/JP2016/079357 filed on Oct. 3, 2016 which designates the United States, incorporated herein by reference, and which claims the benefit of priority from Japanese Patent Application No. 2015-235180, filed on Dec. 1, 2015, incorporated herein by reference.

BACKGROUND

The present disclosure relates to a gaze detection apparatus and a gaze detection method.

Gaze detection apparatuses that detect a position that an operator or a subject gazes at, on an observation surface such as a monitor screen, have been proposed. As a method for detecting a gaze direction of a subject in a non-contact manner without attaching a device to the face, there is a method for irradiating an eyeball of the subject with detection light, calculating a pupil center and a corneal curvature center from an image of the eyeball irradiated with the detection light, and detecting a vector from the corneal curvature center toward the pupil center as the gaze direction of the subject. Conventionally, the gaze direction has been detected on the assumption that the corneal curvature radii have the same value in the right and left eyeballs and the gaze directions are the same in the right and left eyeballs.

Patent Literature 1: Japanese Patent No. 2739331

However, the conventional technology has a problem that accurate detection of the gaze direction is difficult for a subject having substantially different corneal curvature radii in the right and left eyeballs or for a subject having substantially different gaze directions in the right and left eyeballs due to an influence of strabismus or the like.

SUMMARY

It is an object of the present disclosure to at least partially solve the problems in the conventional technology.

The present disclosure includes a light source configured to irradiate an eyeball of a subject with detection light, a position detection unit configured to detect positions of pupil centers indicating centers of pupils of right and left respective eyeballs and positions of corneal reflection centers indicating centers of corneal reflexes of the right and left respective eyeballs from an image of the eyeball irradiated with the detection light, a curvature radius calculation unit configured to calculate corneal curvature radii of the right and left respective eyeballs from a position of the light source and the positions of the corneal reflection centers, a gaze detection unit configured to detect gaze directions of the right and left respective eyeballs from the positions of the pupil centers and the corneal curvature radii, a viewpoint detection unit configured to detect viewpoints of the right and left respective eyeballs from the gaze directions detected in the gaze detection unit, an output control unit configured to display the viewpoints of the right and left respective eyeballs on a display unit from the gaze directions detected in the gaze detection unit, and a determination unit configured to determine whether the right and left eyeballs face a target direction from the gaze directions detected in the gaze detection unit.

The above and other objects, features, advantages and technical and industrial significance of the disclosure will be better understood by reading the following detailed description of presently preferred embodiments of the disclosure, when considered in connection with the accompanying drawings.

DETAILED DESCRIPTION

Figure 1:
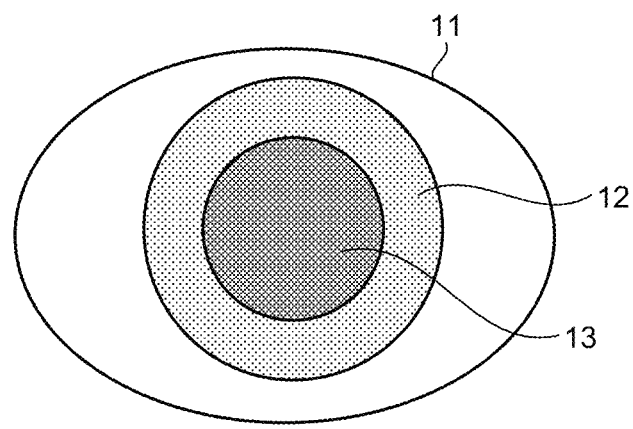
FIG. 1 is a diagram illustrating a state of an eye of a subject in a case of using one light source.

Hereinafter, an embodiment of a gaze detection apparatus and a gaze detection method according to the present disclosure will be described in detail with reference to the drawings. Note that the present disclosure is not limited by this embodiment. Hereinafter, an example of using a gaze detection apparatus for a diagnosis support apparatus that supports diagnosis of strabismus or the like, using a gaze detection result, will be described. Applicable apparatuses are not limited to diagnosis support apparatuses.

Corneal curvature radii may be substantially different in right and left eyeballs or gaze directions may be substantially different in the right and left eyeballs due to an influence of strabismus or the like depending on a subject. The diagnosis support apparatus of the present embodiment can appropriately detect viewpoints of various subjects by individually obtaining corneal curvature radiuses of right and left eyeballs, and further individually detecting viewpoints of the right and left eyeballs of the subject with respect to a monitor screen.

The gaze detection apparatus of the present embodiment detects gaze using illumination units installed at two places. Further, the gaze detection apparatus of the present embodiment calculates a position of a corneal curvature center and a corneal curvature radius with high precision using a result measured by causing the subject to gaze at one point before detecting the gaze.

Note that the illumination unit is an element including a light source and capable of irradiating the eyeball of the subject with light. The light source is an element that generates light, such as a light emitting diode (LED), for example. The light source may be constituted by one LED, or may be constituted by a combination of a plurality of LEDs arranged in one place. Hereinafter, the "light source" may be used as a term expressing the illumination unit.

To detect the viewpoint with high precision, properly detecting a position of a pupil is important. It is known that, in the case of turning on a near-infrared light source and performing a capture with a camera, the pupil becomes darker than other portions when the camera and the light source are separated by a certain distance. The pupil position is detected using this characteristic.

In the present embodiment, with respect to two cameras, two light sources are arranged outside the respective cameras. Then, the two light sources are turned on at different timings from each other, and the camera at a longer distance (more distant) from the lit light source performs a capture. With the capture, the pupil can be more darkly captured and can be distinguished from other portions with high precision.

In this case, the light source to be turned on is different, and thus three-dimensional measurement by an ordinary stereo method cannot be simply applied. That is, a straight line connecting the light source and corneal reflex in obtaining the viewpoint cannot be calculated by world coordinates. Therefore, in the present embodiment, the mutual positional relationship between the cameras used for capture and the mutual positional relationship between the light sources to be turned on at the two timings are made symmetrical with respect to a virtual light source position representing a position of a virtual light source. Then, two coordinate values obtained at respective times of turning on the two light sources are converted into the world coordinates as a coordinate value by a left camera and a coordinate value by a right camera. With the process, the straight line connecting the virtual light source and the corneal reflex can be calculated by the world coordinates, and the viewpoint can be calculated on the basis of the straight line, using the positions of the corneal reflex obtained at the respective times of turning on the two light sources.

Figure 2:
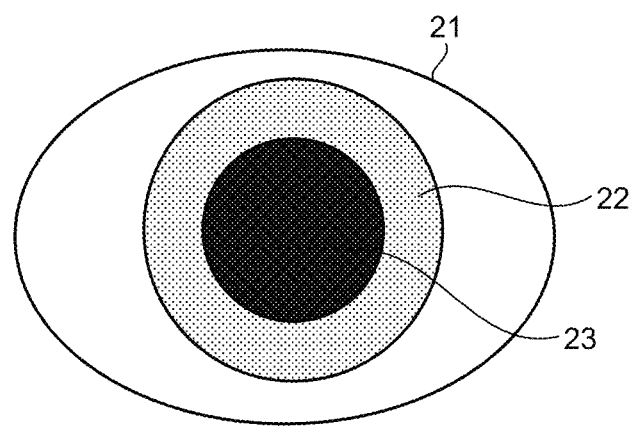
FIG. 2 is a diagram illustrating a state of an eye of a subject in a case of using two light sources.

FIG. 1 is a diagram illustrating a state of an eye 11 of a subject in a case of using one light source. As illustrated in FIG. 1, a difference in darkness between an iris 12 and a pupil 13 is not sufficient, and distinguishing the iris 12 from the pupil 13 is difficult. FIG. 2 is a diagram illustrating a state of an eye 21 of a subject in a case of using two light sources. As illustrated in FIG. 2, a difference in darkness between an iris 22 and a pupil 23 is larger than that in FIG. 1.

Figure 3:
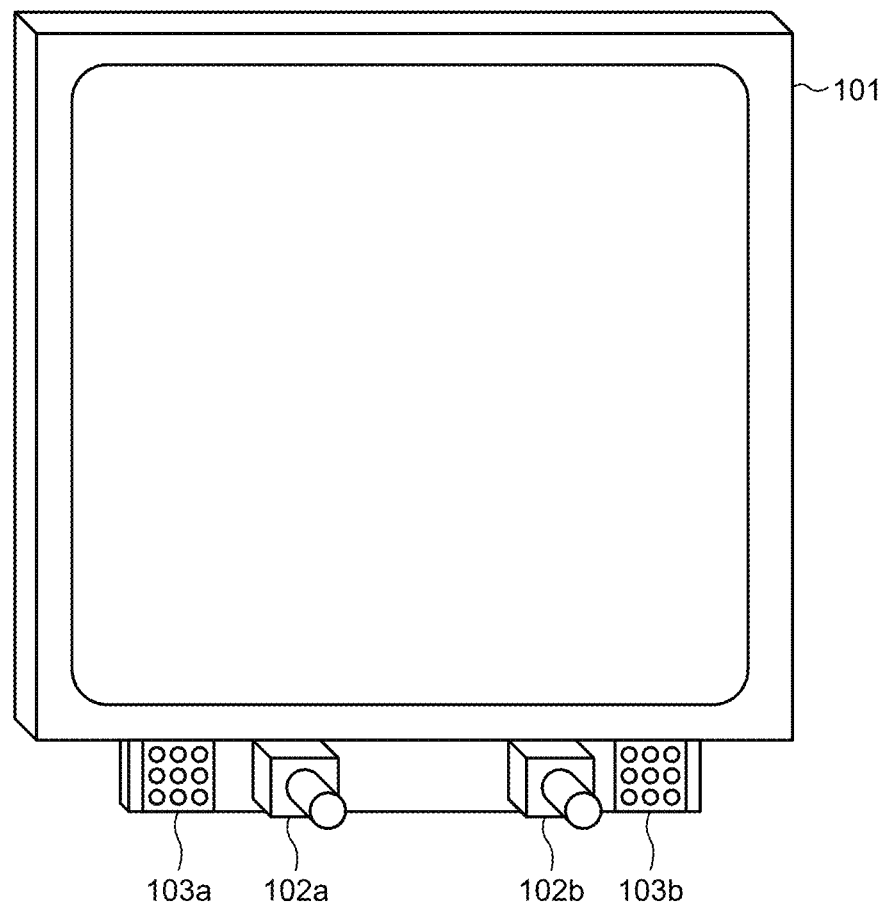
FIG. 3 is a diagram illustrating an example of arrangement of a display unit, a stereo camera, an infrared light source, and a subject of the present embodiment.
Figure 4:
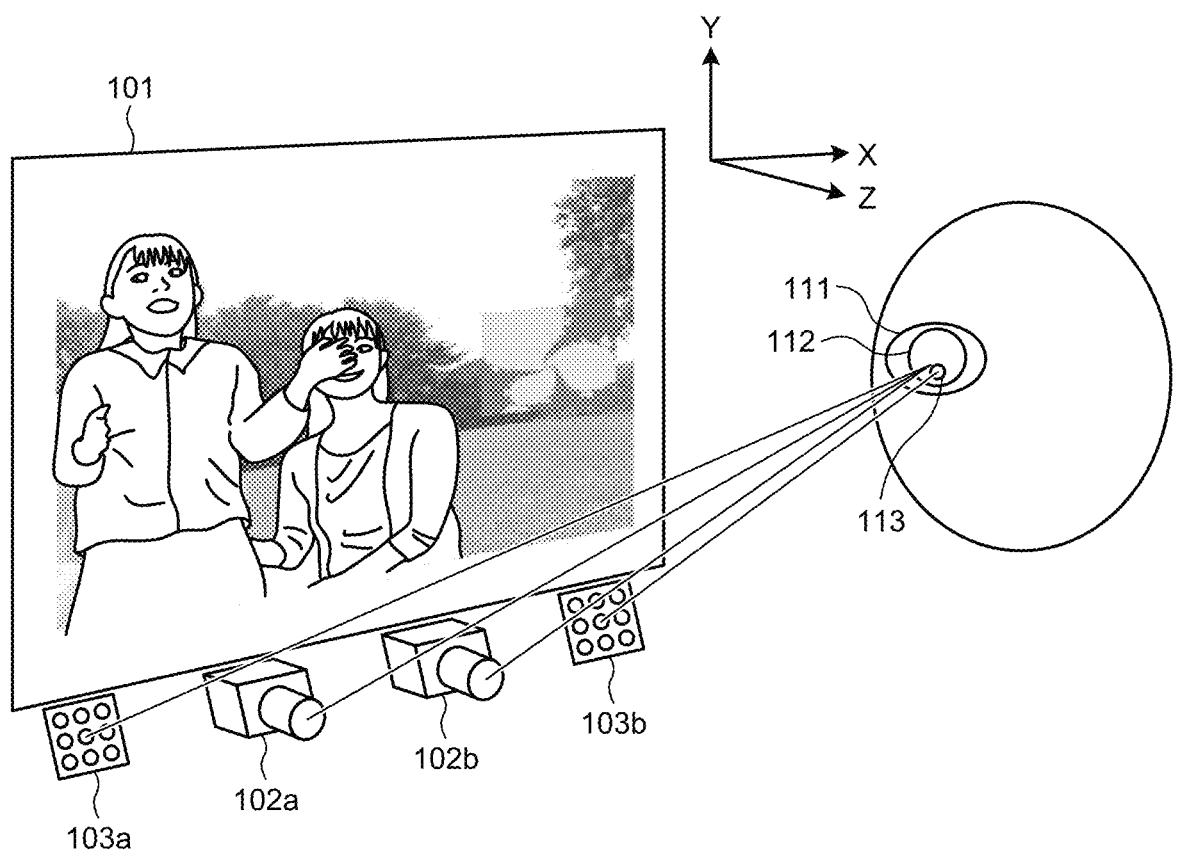
FIG. 4 is a diagram illustrating an example of arrangement of a display unit, a stereo camera, an infrared light source, and a subject of the present embodiment.

FIGS. 3 and 4 are diagrams illustrating examples of arrangement of a display unit, a stereo camera, an infrared light source, and a subject of the present embodiment.

As illustrated in FIG. 3, the diagnosis support apparatus of the present embodiment includes a display unit 101, a right camera 102a and a left camera 102b constituting a stereo camera, and LED light sources 103a and 103b. The right camera 102a and the left camera 102b are arranged under the display unit 101. The LED light sources 103a and 103b are arranged outside the right camera 102a and the left camera 102b, respectively. The LED light sources 103a and 103b are light sources that radiate near-infrared rays having a wavelength of 850 nm, for example. FIG. 3 illustrates an example in which nine LEDs constitute each of the LED light sources 103a and 103b. A lens capable of transmitting the near-infrared light having a wavelength of 850 [nm] is used for the right camera 102a and the left camera 102b. Note that the positions of the LED light sources 103a and 103b and the positions of the right camera 102a and the left camera 102b may be switched, and the LED light sources 103a and 103b may be arranged at inner positions of the right camera 102a and the left camera 102b, respectively.

As illustrated in FIG. 4, the LED light sources 103a and 103b irradiate an eyeball 111 of the subject with the near-infrared light as detection light. The left camera 102b performs a capture when light of the LED light source 103a is radiated, and the right camera 102a performs a capture when light of the LED light source 103b is radiated. By appropriately setting the positional relationship between the right camera 102a and the left camera 102b and the LED light sources 103a and 103b, a pupil 112 is reflected with low luminance and becomes dark and corneal reflex 113, which is caused as a virtual image in the eyeball 111, is reflected with high luminance and becomes bright, in a captured image. Therefore, the positions on the image of the pupil 112 and corneal reflex 113 can be acquired by the two cameras (the right camera 102a and the left camera 102b).

Further, three-dimensional world coordinate values of the positions of the pupil 112 and the corneal reflex 113 are calculated from the positions of the pupil 112 and the corneal reflex 113 obtained by the two cameras. In the present embodiment, as the three-dimensional world coordinates, a center position of a screen of the display unit 101 is set to an origin, an up and down direction represents a Y coordinate (the up direction is +), a cross direction represents an X coordinate (the observers' right is +), and a depth direction represents a Z coordinate (the front side is +).

Figure 5:
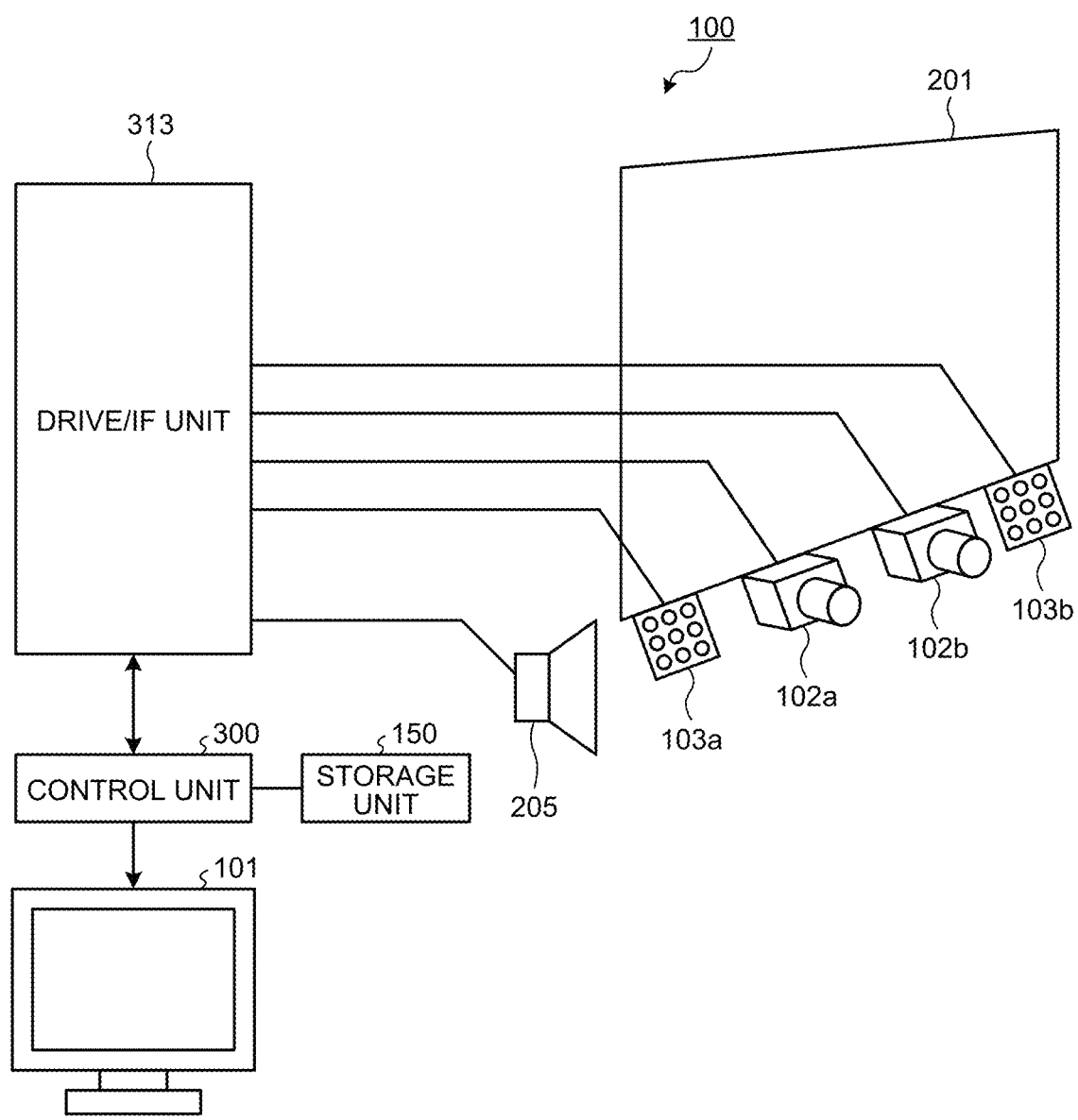
FIG. 5 is a diagram illustrating an outline of functions of a diagnosis support apparatus.

FIG. 5 is a diagram illustrating an outline of functions of a diagnosis support apparatus 100. FIG. 5 illustrates part of the configurations illustrated in FIGS. 3 and 4 and configurations used to drive the configurations. As illustrated in FIG. 5, the diagnosis support apparatus 100 includes the right camera 102a, the left camera 102b, the LED light source 103a for the left camera 102b, the LED light source 103b for the right camera 102a, a speaker 205, a drive/interface (IF) unit 313, a control unit 300, a storage unit 150, and the display unit 101. In FIG. 5, a display screen 201 illustrates the positional relationship between the right camera 102a and the left camera 102b in an easy-to-understand manner. The display screen 201 is a screen displayed on the display unit 101. Note that the drive unit and the IF unit may be integrated or may be separate units.

The speaker 205 functions as a sound output unit that outputs a sound or the like for calling attention to the subject at the time of calibration or the like.

The drive/IF unit 313 drives the units included in the stereo camera. Further, the drive/IF unit 313 is an interface between the units included in the stereo camera and the control unit 300.

The control unit 300 can be realized by a computer including a control device such as a central processing unit (CPU), a storage device such as a read only memory (ROM) and a random access memory (RAM), a communication IF connected to a network and performing communication, and a bus connecting the devices and units.

The storage unit 150 stores various types of information such as a control program, a measurement result, and a diagnosis support result. The storage unit 150 stores an image to be displayed on the display unit 101, and the like, for example. The display unit 101 displays various types of information such as a target image for diagnosis.

Figure 6:
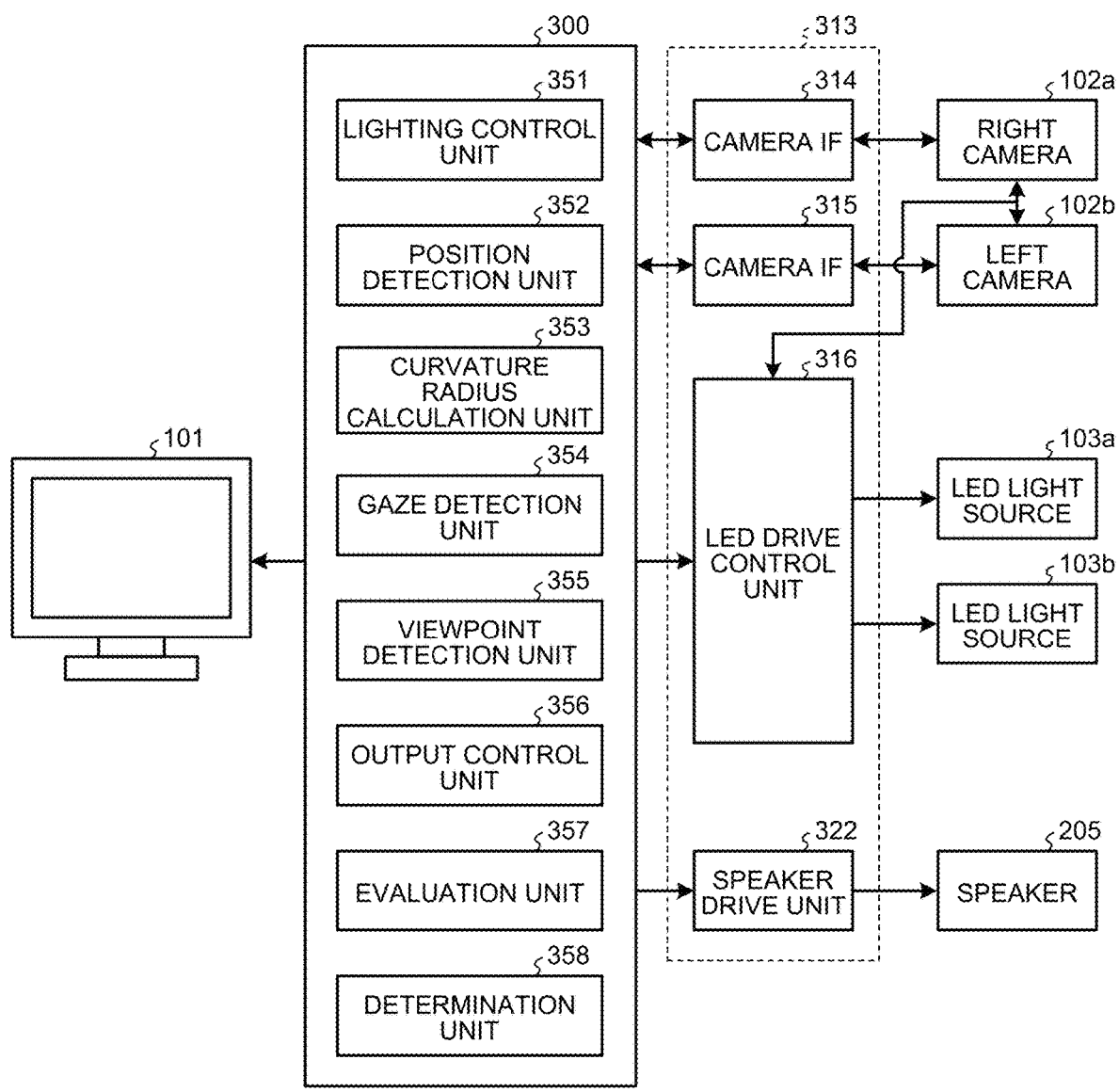
FIG. 6 is a block diagram illustrating an example of detailed functions of units illustrated in FIG. 5.

FIG. 6 is a block diagram illustrating an example of detailed functions of the units illustrated in FIG. 5. As illustrated in FIG. 6, the display unit 101 and the drive/IF unit 313 are connected to the control unit 300. The drive/IF unit 313 includes camera IFs 314 and 315, an LED drive control unit 316, and a speaker drive unit 322.

The right camera 102*a* and the left camera 102*b* are connected to the drive/IF unit 313 via the camera IFs 314 and 315, respectively. The drive/IF unit 313 drives these cameras to image the subject. A frame synchronization signal is output from the right camera 102*a*. The frame synchronization signal is input to the left camera 102*b* and the LED drive control unit 316. As a result, the LED light sources 103*a* and 103*b* are emitted, and images by the right and left cameras are taken in corresponding to the light emission.

The speaker drive unit 322 drives the speaker 205. Note that the diagnosis support apparatus 100 may include an interface (printer IF) for being connected with a printer as a printing unit. Further, a printer may be provided inside the diagnosis support apparatus 100.

The control unit 300 controls the entire diagnosis support apparatus 100. The control unit 300 includes a lighting control unit 351, a position detection unit 352, a curvature radius calculation unit 353, a gaze detection unit 354, a viewpoint detection unit 355, an output control unit 356, an evaluation unit 357, and a determination unit 358.

The elements (the lighting control unit 351, the position detection unit 352, the curvature radius calculation unit 353, the gaze detection unit 354, the viewpoint detection unit 355, the output control unit 356, the evaluation unit 357, and the determination unit 358) included in the control unit 300 may be realized by software (a program), by a hardware circuit, or by use of software and a hardware circuit in combination.

In the case of realizing the elements by a program, the program is recorded in an installable format file or an executable format file in a computer-readable recording medium such as a compact disk read only memory (CD-ROM), a flexible disk (FD), a compact disk recordable (CD-R), or a digital versatile disk (DVD), and is provided as a computer program product. The program may be stored on a computer connected to a network such as the Internet and provided by being downloaded via the network. Alternatively, the program may be provided or distributed via a network such as the Internet. Alternatively, the program may be provided by being incorporated in a ROM or the like in advance.

The lighting control unit 351 controls lighting of the LED light sources 103*a* and 103*b*, using the LED drive control unit 316. For example, the lighting control unit 351 controls the LED light sources 103*a* and 103*b* to be turned on at different timings from each other. The timing difference (time) may be a time determined in advance as a time during which an influence is not caused on a gaze detection result due to movement of the gaze of the subject or the like.

The position detection unit 352 detects pupil areas indicating pupils of right and left respective eyeballs, and corneal reflex areas indicating corneal reflexes of the right and left respective eyeballs, from images of the right and left eyeballs of the subject imaged by the stereo camera after the right and left eyeballs are irradiated with near-infrared light. Further, the position detection unit 352 detects positions of pupil centers indicating centers of the pupils of the right and left respective eyeballs on the basis of the pupil areas. For example, the position detection unit 352 selects a plurality of points on a contour of the pupil area, and calculates a center of a circle passing through the plurality of selected points as the position of the pupil center. Similarly, the position detection unit 352 detects positions of corneal reflection centers indicating centers of the corneal reflexes of the right and left respective eyeballs on the basis of the corneal reflex areas.

The curvature radius calculation unit 353 calculates a position of a corneal curvature center from a first straight line connecting a virtual light source position and the corneal reflection center. Further, the curvature radius calculation unit 353 calculates corneal curvature radii that are distances between corneal surfaces and the corneal curvature centers of the right and left respective eyeballs of the subject, from the virtual light source position and the positions of the corneal reflection centers.

The curvature radius calculation unit 353 calculates an intersection point of a second straight line connecting the pupil center and the target position and the first straight line connecting the corneal reflection center and the virtual light source position, using the pupil center and the corneal reflection center calculated when the subject is caused to gaze at the target position. The calculated intersection point is the corneal curvature center. The curvature radius calculation unit 353 calculates a distance between the pupil center and the corneal curvature center, and stores the distance in the storage unit 150. Further, the curvature radius calculation unit 353 calculates the corneal curvature radius that is the distance between the corneal surface and the corneal curvature center, and stores the corneal curvature radius in the storage unit 150.

The target position may be determined in advance, and any position may be employed as long as the three-dimensional world coordinate values can be calculated. For example, a center position of the display screen 201 (the origin of three-dimensional world coordinates) can be set as the target position. In this case, for example, the output control unit 356 displays a target image or the like that the subject gazes at, at the target position (center position) on the display screen 201. With the display, the subject can gaze at the target position.

The target image may be any image as long as the image can attract the subject's attention. For example, an image with a display mode such as luminance and color that changes, or an image with a display mode that is different from other areas can be used as the target image.

Note that the target position is not limited to the center position of the display screen 201 and may be any position. If the center position of the display screen 201 is set as the target position, the distance to an arbitrary end portion of the display screen 201 becomes minimum. Therefore, a measurement error at the time of detecting the gaze can be further reduced, for example.

The processing up to the calculation of the distance between the pupil center and the corneal curvature center and the calculation of the corneal curvature radius is executed in advance by the time of the start of actual gaze detection, for example. At the time of detecting the gaze, the curvature radius calculation unit 353 can calculate a position where the distance from the pupil center becomes the distance calculated in advance, on the first straight line connecting the virtual light source position and the corneal reflection center, as the corneal curvature center. The curvature radius calculation unit 353 calculates the position of the corneal curvature center from the virtual light source position, a predetermined position indicating the target image on the display unit, the position of the pupil center, and the position of the corneal reflection center, and calculates the corneal curvature radius.

The gaze detection unit 354 detects gaze directions of the right and left respective eyeballs of the subject from the positions of the pupil centers, and the positions of the corneal curvature radii or of the corneal curvature centers. For example, the gaze detection unit 354 detects a direction from the corneal curvature center to the pupil center as the gaze direction of the subject.

The viewpoint detection unit 355 detects viewpoints of the right and left respective eyeballs of the subject from the gaze directions detected by the gaze detection unit 354. The viewpoint detection unit 355 detects, for example, a viewpoint (gaze point) that the subject gazes on the display screen 201. The viewpoint detection unit 355 detects an intersection point between a gaze vector expressed by a three-dimensional world coordinate system as illustrated in FIG. 2 and an XY plane, as the viewpoint of the subject.

The output control unit 356 controls outputs of various types of information to the display unit 101, the speaker 205, and the like. In the present embodiment, the output control unit 356 causes the display unit 101 to display the gaze directions of the right and left respective eyeballs of the subject. The output control unit 356 causes the display unit 101 to display the viewpoints of the right and left respective eyeballs detected by the viewpoint detection unit 355, using the gaze directions detected by the gaze detection unit 354. Further, the output control unit 356 causes the target image to be output to the target position on the display unit 101. Further, the output control unit 356 controls outputs to the display unit 101, such as a diagnostic image and an evaluation result by the evaluation unit 357.

The evaluation unit 357 evaluates respective states of the right and left eyeballs from movement loci of the viewpoints of the right and left respective eyeballs. For example, the evaluation unit 357 evaluates ways of movement of the right and left eyeballs and evaluates whether one of the right and left eyeballs has strabismus, from the movement loci of the viewpoints of the right and left respective eyeballs.

The determination unit 358 determines whether the right and left respective eyeballs face a target direction, from the gaze directions detected by the gaze detection unit 354 or the viewpoints detected by the viewpoint detection unit 355. For example, the determination unit 358 determines whether the right and left eyeballs face the target direction on the basis of at least one of a first movement locus of the viewpoint of the left eyeball and a second movement locus of the viewpoint of the right eyeball. The target direction herein refers to a direction in which the right and left eyeballs move along a target locus described below.

Figure 7:
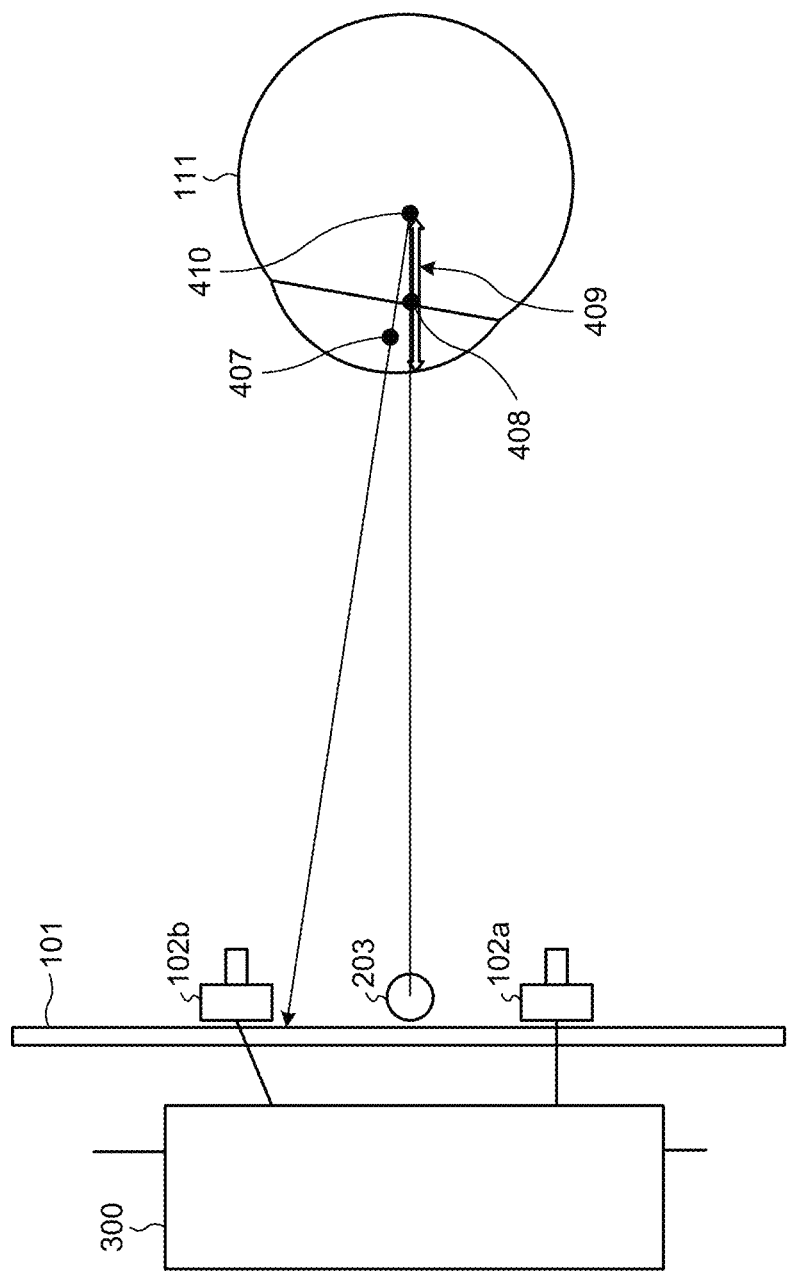
FIG. 7 is a diagram for describing an outline of processing in a case of assuming that one light source is used.

FIG. 7 is a diagram for describing an outline of processing in a case of assuming that one light source is used. The same reference numerals are given to elements that have been described in FIGS. 3 to 6, and description of the elements is omitted. In the example of FIG. 7, one LED light source 203 is used in place of the two LED light sources 103*a* and 103*b*.

A pupil center 407 and a corneal reflection center 408 respectively represent the pupil center and the corneal reflection center detected when the one LED light source 203 is turned on. The corneal reflection center 408 exists on a straight line connecting the LED light source 203 and a corneal curvature center 410, and the position of the corneal reflection center 408 appears at a midpoint between the corneal curvature center 410 and the corneal surface. A corneal curvature radius 409 represents the distance from the corneal surface to the corneal curvature center 410. Although the LED light source 203 is one LED here, a combination of several small LEDs may be arranged at one place.

Figure 8:
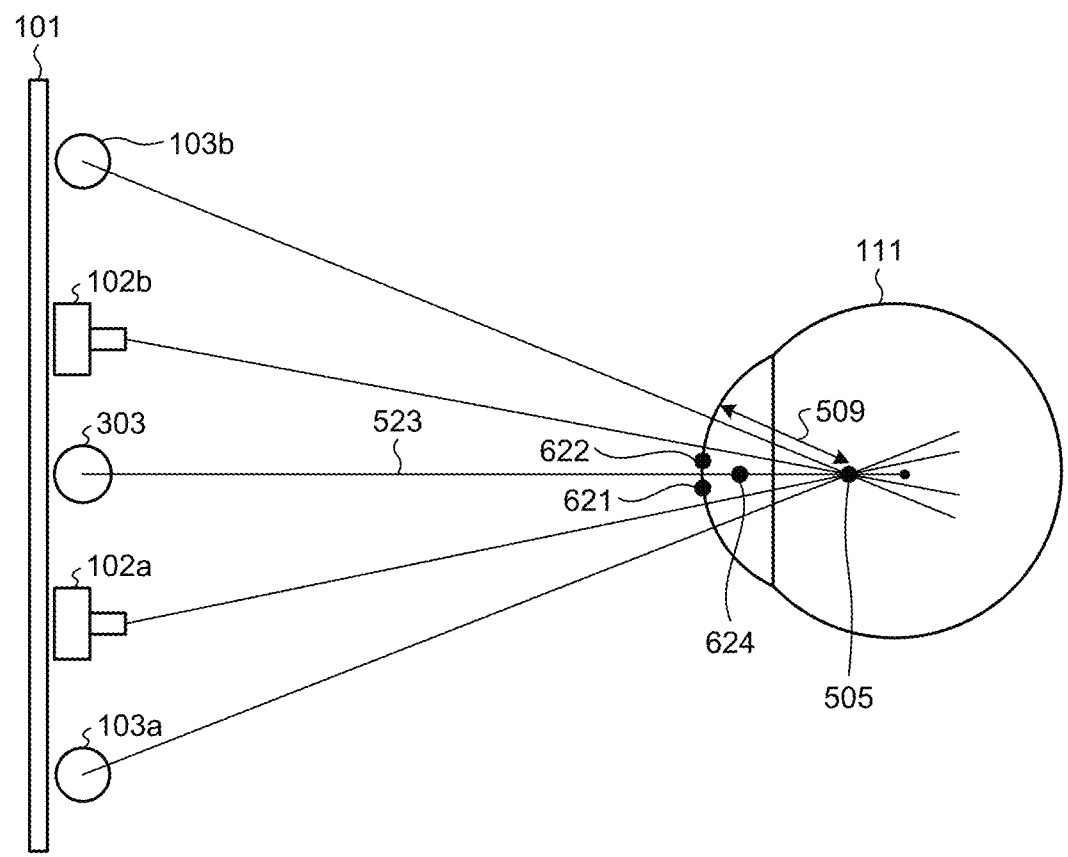
FIG. 8 is a diagram for describing an outline of processing executed by the diagnosis support apparatus of the present embodiment.

FIG. 8 is a diagram for describing an outline of processing executed by the diagnosis support apparatus 100 of the present embodiment. The same reference numerals are given to elements that have been described in FIGS. 3 to 6, and description of the elements is omitted.

A corneal reflection point 621 represents a corneal reflection point on an image when the left camera 102*b* captures the image. A corneal reflection point 622 represents a corneal reflection point on an image when the right camera 102*a* captures the image. In the present embodiment, the right camera 102*a* and the LED light source 103*b* for the right camera, and the left camera 102*b* and the LED light source 103*a* for the left camera are in a right and left symmetrical positional relationship with respect to a straight line passing through an intermediate position between the right camera 102*a* and the left camera 102*b*. Therefore, a virtual light source 303 can be regarded to be at the intermediate position (virtual light source position) between the right camera 102*a* and the left camera 102*b*. A corneal reflection point 624 represents a corneal reflection point corresponding to the virtual light source 303. World coordinate values of the corneal reflection point 624 is calculated by converting a coordinate value of the corneal reflection point 621 and a coordinate value of the corneal reflection point 622, using conversion parameters for converting coordinate values of the right and left cameras into three-dimensional world coordinates. A corneal curvature center 505 exists on a straight line 523 connecting the virtual light source 303 and the corneal reflection point 624. When the position of the corneal curvature center 505 and the position of the corneal surface are calculated, a corneal curvature radius 509 is calculated. In this manner, viewpoint detection can be performed by an equivalent method to the gaze detection method using the light source at one place illustrated in FIG. 7.

Note that the positional relationship between the right camera 102*a* and the left camera 102*b* and the positional relationship between the LED light source 103*a* and the LED light source 103*b* are not limited to the above-described positional relationships. For example, the positional relationships may be right and left symmetrical with respect to the same straight line, or the right camera 102*a* and the left camera 102*b*, and the LED light source 103*a* and the LED light source 103*b* may not be on the same straight line.

Figure 9:
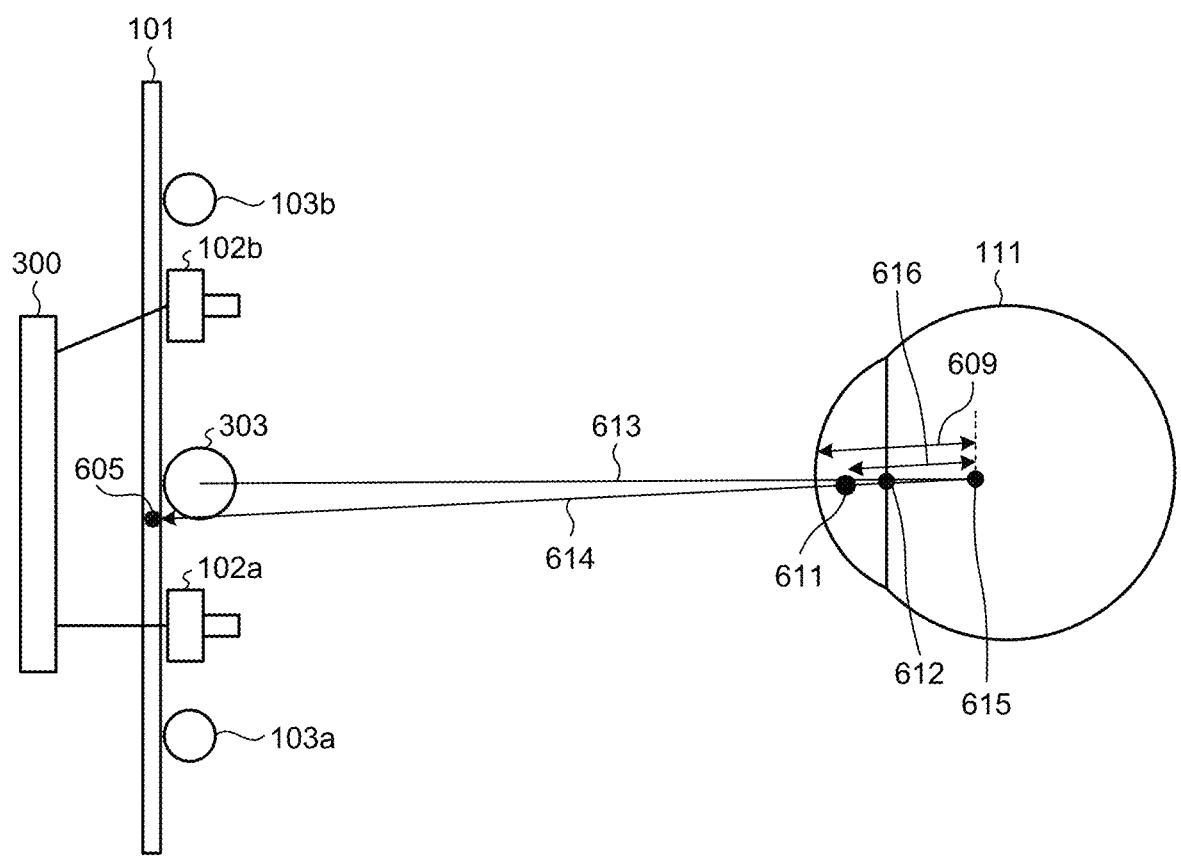
FIG. 9 is a diagram for describing calibration processing for calculating a distance between a pupil center position and a corneal curvature center position.

FIG. 9 is a diagram for describing calibration processing for calculating a position of a corneal curvature center 615, and a distance 616 between a position of a pupil center 611 and the position of the corneal curvature center 615, before gaze detection or viewpoint detection is performed. The same reference numerals are given to elements that have been described in FIGS. 3 to 6, and description of the elements is omitted.

A target position 605 is a position that is one point on the display unit 101, where the target image or the like is output and the subject gazes at the target image. In the present embodiment, the target position 605 is a center position on a screen of the display unit 101. A straight line 613 is a straight line connecting the virtual light source 303 and a corneal reflection center 612. A straight line 614 is a straight line connecting the target position 605, which is a gaze point that the subject gazes at, and the pupil center 611. The corneal curvature center 615 is an intersection point of the straight line 613 and the straight line 614. A corneal curvature radius 609 is a distance between the corneal surface and the corneal curvature center 615. The curvature radius calculation unit 353 calculates the distance 616 between the pupil center 611 and the corneal curvature center 615, and the corneal curvature radius 609, and stores the calculated distance and radius in the storage unit 150.

Figure 10:
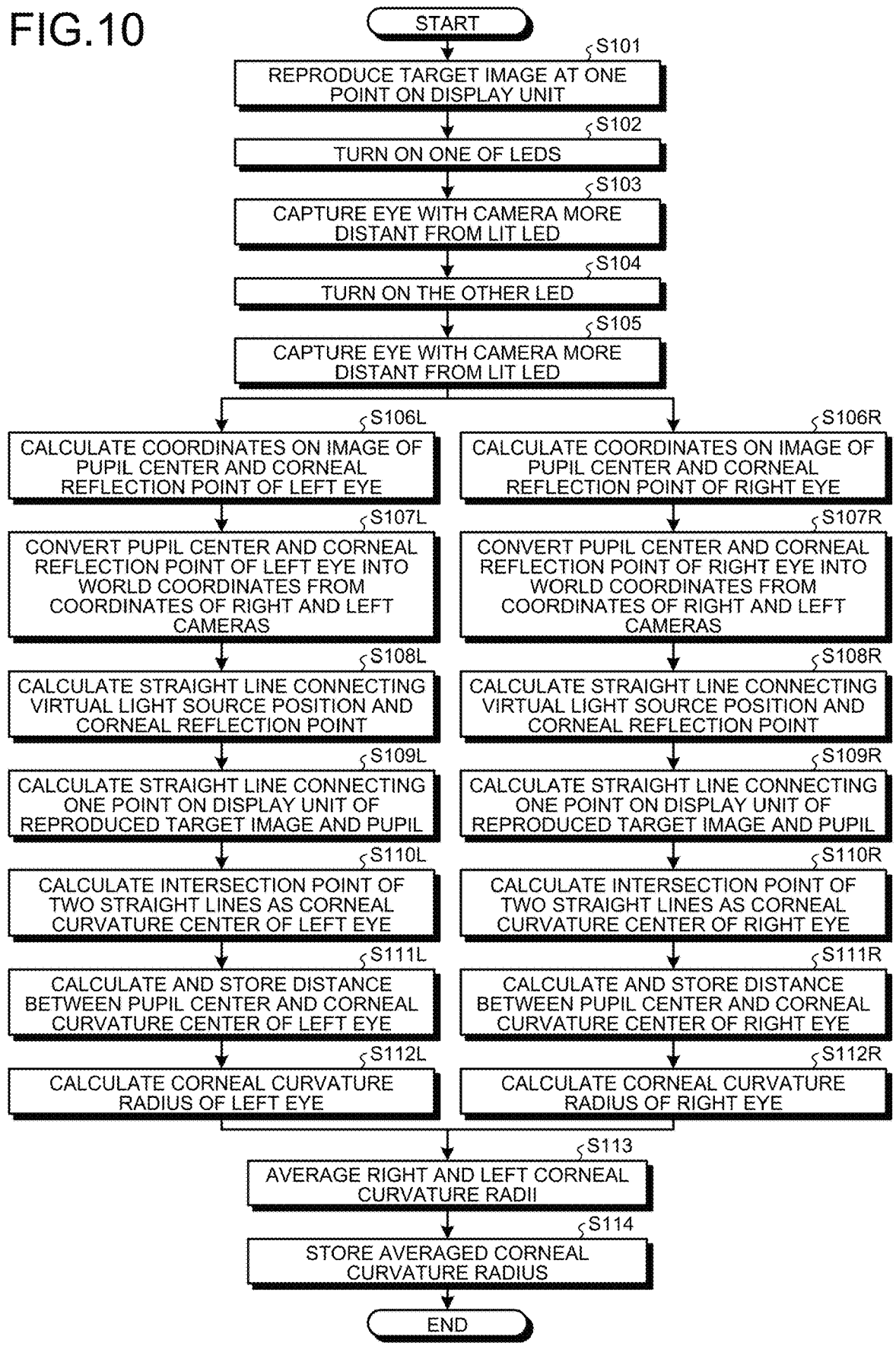
FIG. 10 is a flowchart illustrating an example of the calibration processing of the present embodiment.

FIG. 10 is a flowchart illustrating an example of the calibration processing of the present embodiment. The output control unit 356 reproduces the target image at one point on the screen of the display unit 101 (Step S101), and causes the subject to gaze at the one point. Next, the lighting control unit 351 turns on one of the LED light sources 103a and 103b toward the eye of the subject, using the LED drive control unit 316 (Step S102). The control unit 300 captures an image of the subject's eye with a camera having a longer distance from the lit LED light source between the right and left cameras (the right camera 102a and the left camera 102b) (Step S103). Next, the lighting control unit 351 turns on the other of the LED light sources 103a and 103b toward the eye of the subject (Step S104). The control unit 300 captures an image of the subject's eye with a camera having a longer distance from the lit LED light source between the right and left cameras (Step S105).

Note that it is not necessary to stop imaging by a camera other than the camera having a longer distance from the lit LED light source. That is, it is sufficient if the subject's eye is imaged with at least the camera having a longer distance from the lit LED light source, and the captured image can be used for coordinate calculation or the like.

After Step S105, processing for the left eye that is the left eyeball and processing for the right eye that is the right eyeball are separately performed. First, the calibration processing for the left eye will be described.

The pupil area of the left eye is detected as a dark part (dark pupil) by irradiation by the LED light source 103a or the LED light source 103b. As reflection of LED irradiation, a virtual image of corneal reflex of the left eye is generated, and a corneal reflection point (corneal reflection center) is detected as a bright part. That is, the position detection unit 352 detects the pupil area of the left eye from the captured image, and calculates coordinates indicating the position of the pupil center of the left eye. For example, the position detection unit 352 detects an area having predetermined brightness or less including a darkest part in a certain area including the left eye, as the pupil area, and detects an area having predetermined brightness or more including a brightest part, as the corneal reflex. Further, the position detection unit 352 detects the corneal reflex area of the left eye from the captured image, and calculates coordinates indicating the position of the corneal reflection center. Note that the position detection unit 352 calculates the coordinate value of the pupil center and the coordinate value of the corneal reflection center of the left eye, for each of the two images acquired with the right and left cameras (Step S106L).

Note that, to acquire three-dimensional world coordinates, the right and left cameras are calibrated by a stereo calibration method in advance, and conversion parameters are calculated. As the stereo calibration method, any conventional method such as a method using Tsai's camera calibration theory can be applied.

The position detection unit 352 converts the pupil center and the corneal reflection center of the left eye from the coordinates of the right and left cameras to three-dimensional world coordinates, using the conversion parameters (Step S107L). For example, the position detection unit 352 performs the conversion into the three-dimensional world coordinates using the conversion parameters, setting coordinates obtained from an image captured by the left camera 102b when the LED light source 103a is turned on as the coordinates of the left camera, and setting coordinates obtained from an image captured by the right camera 102a when the LED light source 103b is turned on as the coordinates of the right camera. The world coordinate value obtained as a result of the conversion corresponds to the world coordinate value obtained from the images captured by the right and left cameras, assuming that the light is radiated from the virtual light source 303. The curvature radius calculation unit 353 obtains a straight line connecting the obtained world coordinates of the corneal reflection center and the world coordinates of the center position of the virtual light source 303 (Step S108L). Next, the curvature radius calculation unit 353 calculates a straight line connecting the world coordinates of the center of the target image displayed at one point on the screen of the display unit 101 and the world coordinates of the pupil center of the left eye (Step S109L). The curvature radius calculation unit 353 obtains an intersection point of the straight line calculated in Step S108L and the straight line calculated in Step S109L, and sets the intersection point as the corneal curvature center of the left eye (Step S110L). The curvature radius calculation unit 353 calculates the distance between the pupil center and the corneal curvature center at this time and stores the distance in the storage unit 150 (Step S111L). Further, the curvature radius calculation unit 353 calculates the corneal curvature radius of the left eye (Step S112L).

The distance between the pupil center and the corneal curvature center in gazing at one point on the display unit 101 in the calibration processing is kept constant within a range for detecting a viewpoint within the display unit 101. The distance between the pupil center and the corneal curvature center may be obtained from an average of the entire values calculated during reproduction of the target image or may be obtained from an average of several values of the values calculated during the reproduction.

The procedure up to the calculation of the corneal curvature radius of the left eye has been described. A procedure similar to that of Steps S106L to S112L for the left eye is also performed for the right eye (Steps S106R to S112R), and the corneal curvature radius of the right eye is calculated. Description of the procedure up to calculation of the corneal curvature radius of the right eye is omitted.

After calculating the corneal curvature radius of the left eye and the corneal curvature radius of the right eye, the curvature radius calculation unit 353 averages the corneal curvature radii of the right and left eyeballs (Step S113).

That is, the curvature radius calculation unit 353 performs calculation of (r1+r2)/2 to calculate an averaged corneal curvature radius ra, where the corneal curvature radius of the left eye is r1 and the corneal curvature radius of the right eye is r2. The curvature radius calculation unit 353 stores the averaged corneal curvature radius ra in the storage unit 150 (Step S114).

Figure 11:
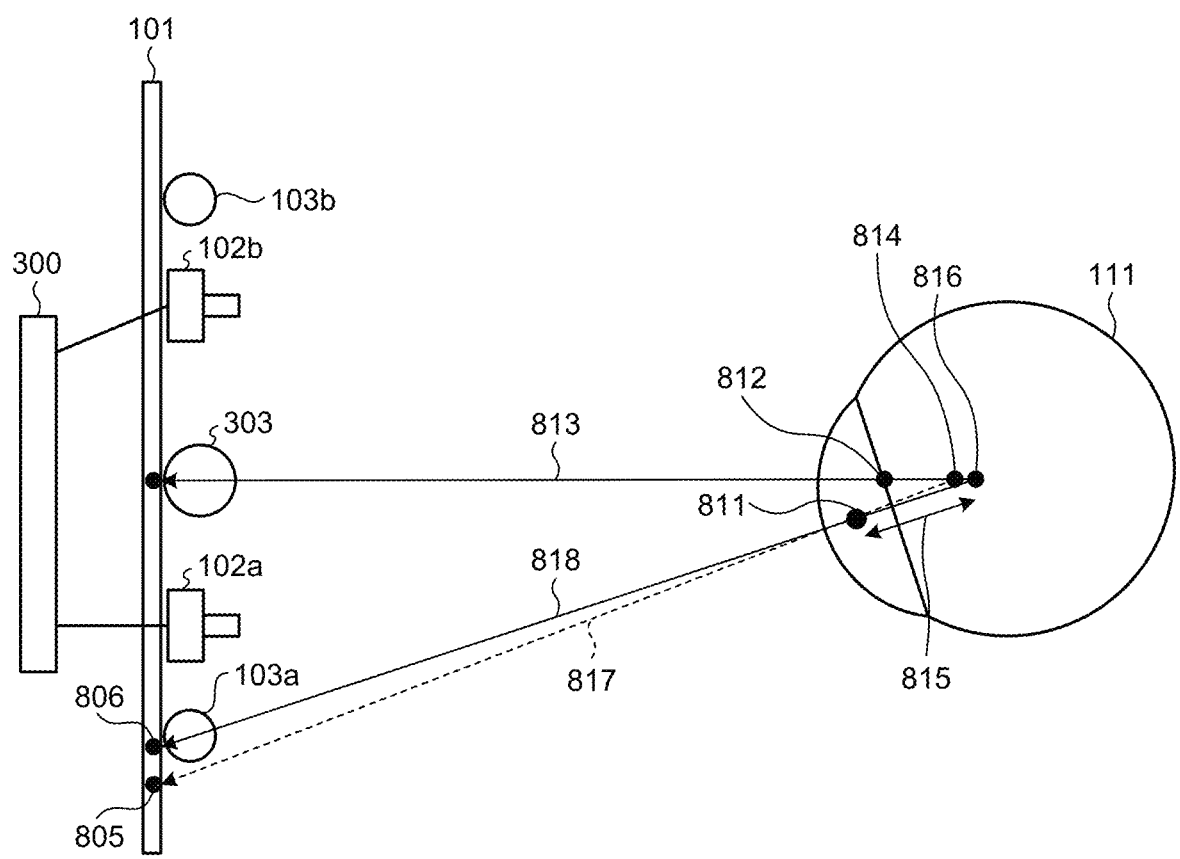
FIG. 11 is a diagram illustrating a method for calculating a position of a corneal curvature center, using the distance obtained in advance.

FIG. 11 is a diagram illustrating a method of calculating a position of a corrected corneal curvature center, using the distance between the pupil center and the corneal curvature center obtained in advance, in performing viewpoint detection. A gaze point 805 represents a gaze point obtained from the corneal curvature center calculated using a general curvature radius value. A gaze point 806 represents a gaze point obtained from the corneal curvature center calculated using a distance obtained in advance.

A pupil center 811 and a corneal reflection center 812 indicate the position of the pupil center and the position of the corneal reflection center calculated at the time of detecting a viewpoint, respectively. A straight line 813 is a straight line connecting the virtual light source 303 and the corneal reflection center 812. A corneal curvature center 814 is the position of the corneal curvature center calculated from a general curvature radius value. A distance 815 is the distance between the pupil center and the corneal curvature center calculated by calibration processing in advance. A corneal curvature center 816 is the position of the corneal curvature center calculated using a distance obtained in advance. The corneal curvature center 816 is obtained from the fact that the corneal curvature center lies on the straight line 813 and that the distance between the pupil center and the corneal curvature center is distance 815. As a result, a gaze 817 calculated using a general curvature radius value is corrected to a gaze 818. Further, the gaze point on the screen of the display unit 101 is corrected from the gaze point 805 to the gaze point 806.

Figure 12:
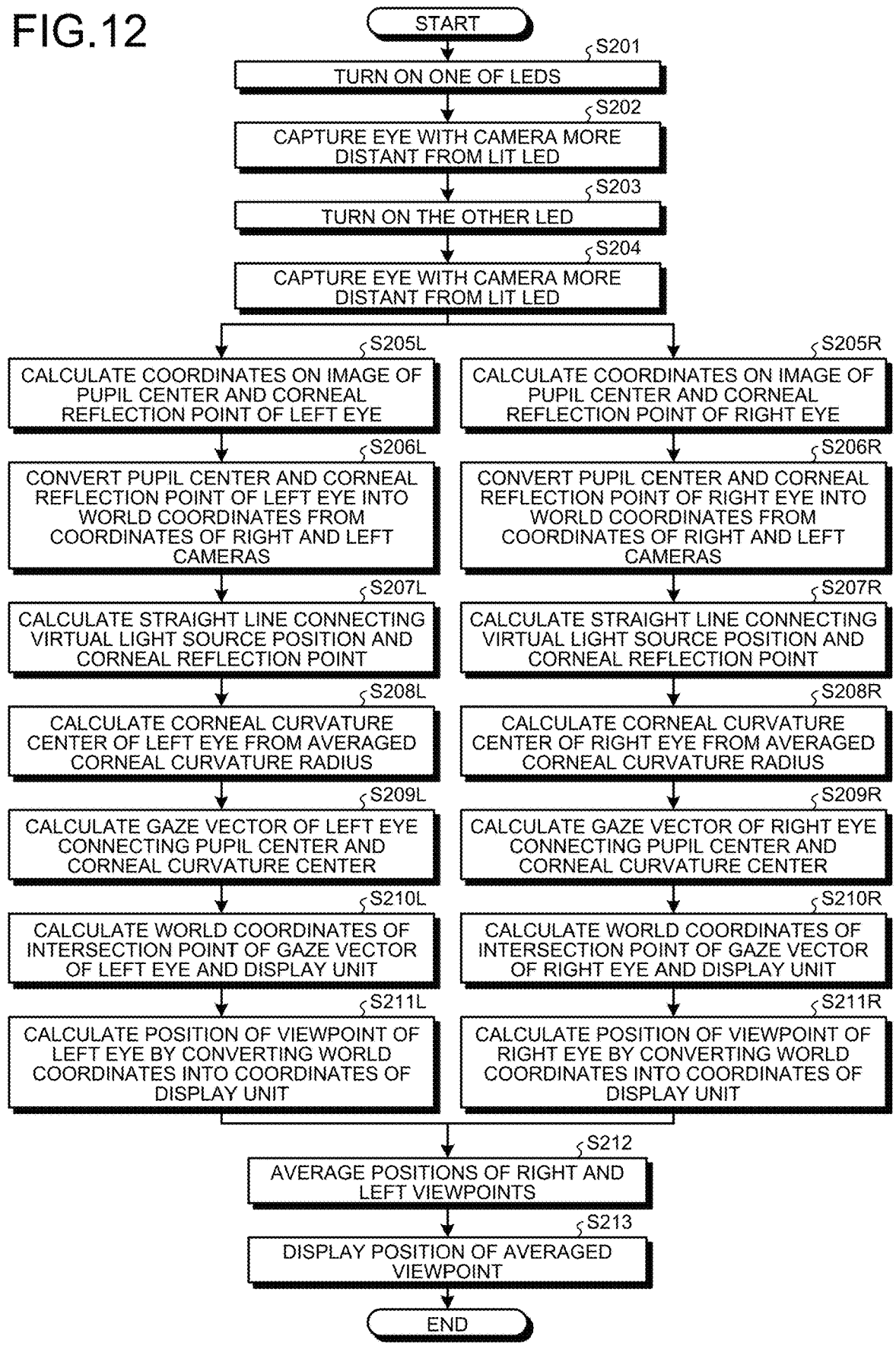
FIG. 12 is a flowchart illustrating an example of gaze detection processing of the present embodiment.

FIG. 12 is a flowchart illustrating an example of gaze detection processing of the present embodiment. First, processing from Steps S201 to S204 illustrated in FIG. 12 is executed. Steps S201 to S204 are similar to Steps S102 to S105 in FIG. 10, and thus description is omitted.

After Step S204, processing for the left eye that is the left eyeball and processing for the right eye that is the right eyeball are separately performed. First, the gaze detection processing for the left eye will be described. Note that processing from Step S205L to Step S207L illustrated in FIG. 12 is similar to the processing from Step S106L to Step S108L in FIG. 10, and thus description is omitted.

The curvature radius calculation unit 353 calculates a position existing on the straight line calculated in Step S207L and equal to the corneal curvature center of the corneal curvature radius ra stored in the storage unit 150 in Step S114 in FIG. 10, as the corneal curvature center of the left eye (Step S208L).

The gaze detection unit 354 obtains a gaze vector connecting the pupil center and the corneal curvature center of the left eye (Step S209L). This vector indicates the gaze direction in which the left eye of the subject views. The viewpoint detection unit 355 calculates a three-dimensional world coordinate value of an intersection point between the gaze direction and the screen of the display unit 101 (Step S210L). This value is a coordinate value representing one point on the display unit 101 that the left eye of the subject gazes at and is expressed by world coordinates. The viewpoint detection unit 355 converts the obtained three-dimensional world coordinate value into coordinate values (x, y) expressed by a two-dimensional coordinate system of the display unit 101 (Step S211L). With the conversion, the viewpoint (gaze point) on the display unit 101 that the left eye of the subject is gazing at, is calculated.

The procedure up to the calculation of the viewpoint of the left eye has been described. A procedure similar to that of Steps S205L to S211L for the left eye is also performed for the right eye (Steps S205R to S211R), and the viewpoint of the right eye is calculated. Description of a procedure up to calculation of a viewpoint of the right eye is omitted.

After calculating the gaze direction and the viewpoint of the left eye and calculating the gaze direction and the viewpoint of the right eye, the viewpoint detection unit 355 averages the viewpoints of the right and left eyeballs (Step S212). That is, the viewpoint detection unit 355 performs calculation of (x1+x2)/2 to calculate an averaged X coordinate xa, and performs calculation of (y1+y2)/2 to calculate an averaged Y coordinate ya, where the coordinate value of the gaze point of the left eye is (x1, y1) and the coordinate value of the gaze point of the right eye is (x2, y2). The output control unit 356 displays the coordinate values (xa, ya) of the averaged viewpoint on the display unit 101 (Step S213).

Figure 13:
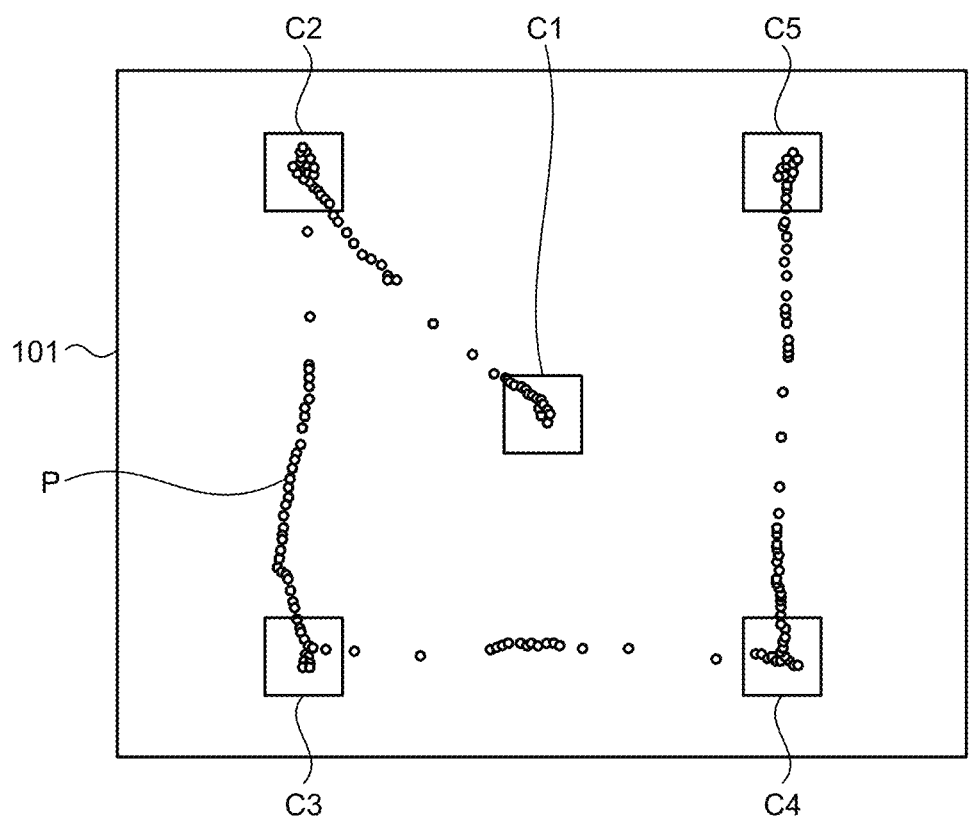
FIG. 13 is a diagram illustrating a display example of a display unit of the present embodiment.

FIG. 13 is a diagram illustrating an example of viewpoints displayed on the display unit 101 by the output control unit 356 in Step S213. As illustrated in FIG. 13, index images C1, C2, C3, C4, and C5 are displayed on the display unit 101. To evaluate how the eyeballs of the subject move, the subject is instructed to move the viewpoints of both the right and left eyeballs in order of the index images C1, C2, C3, C4, and C5.

A plot point P indicating an averaged viewpoint of both the right and left eyeballs is displayed on the display unit 101. After the detection of the viewpoints is performed, an operation input unit provided in the diagnosis support apparatus 100 is operated by an operator or the subject, and the plot point P is displayed on the display unit 101 by the operation. Detection of the viewpoints is performed at a cycle (for example, every 50 [msec]) of frame synchronization signals output from the right and left cameras. Therefore, a larger interval between the plot points P indicates faster movement of the viewpoints.

In the processing described with reference to FIGS. 10 and 12, the corneal curvature radii of the right and left eyeballs are averaged, and the gaze directions or the viewpoints of the right and left eyeballs are averaged. The corneal curvature radii of the right and left eyeballs are averaged on the assumption that the corneal curvature radii have the same value in the right and left eyeballs, and the viewpoints of the right and left eyeballs are averaged on the assumption that the gaze directions of the right and left eyeballs are the same. In the case of a subject having substantially equal corneal curvature radii in the right and left eyeballs or in the case of a subject having substantially equal gaze directions of the right and left eyeballs, the gaze direction can be accurately detected even by the processing described with reference to FIGS. 10 and 12. However, if the corneal curvature radii of the right and left eyeballs are averaged, or the gaze directions or the viewpoints of the right and left eyeballs are averaged, for a subject having substantially different corneal curvature radii (the positions of the corneal curvature centers) in the right and left eyeballs or for a subject having substantially different gaze directions of the right and left eyeballs due to an influence of strabismus or the like, detection of a correct gaze direction or viewpoint is difficult.

Therefore, in the present embodiment, the control unit 300 individually stores the corneal curvature radius of the left eye and the corneal curvature radius of the right eye in the storage unit 150, and individually displays the gaze direction or the viewpoint of the left eye and the gaze direction or the viewpoint of the right eye on the display unit 101.

Figure 14:
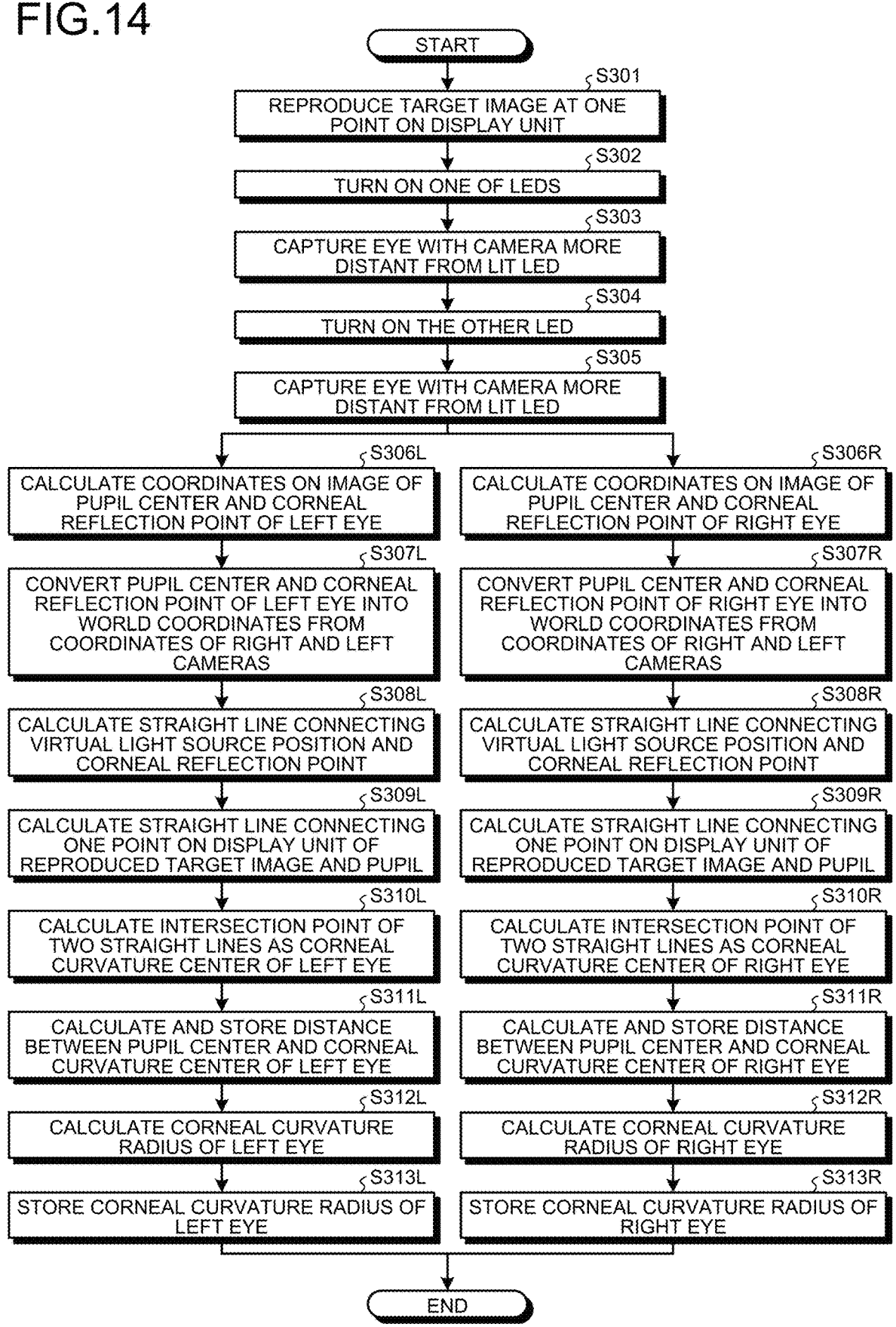
FIG. 14 is a flowchart illustrating an example of the calibration processing of the present embodiment.
Figure 15:
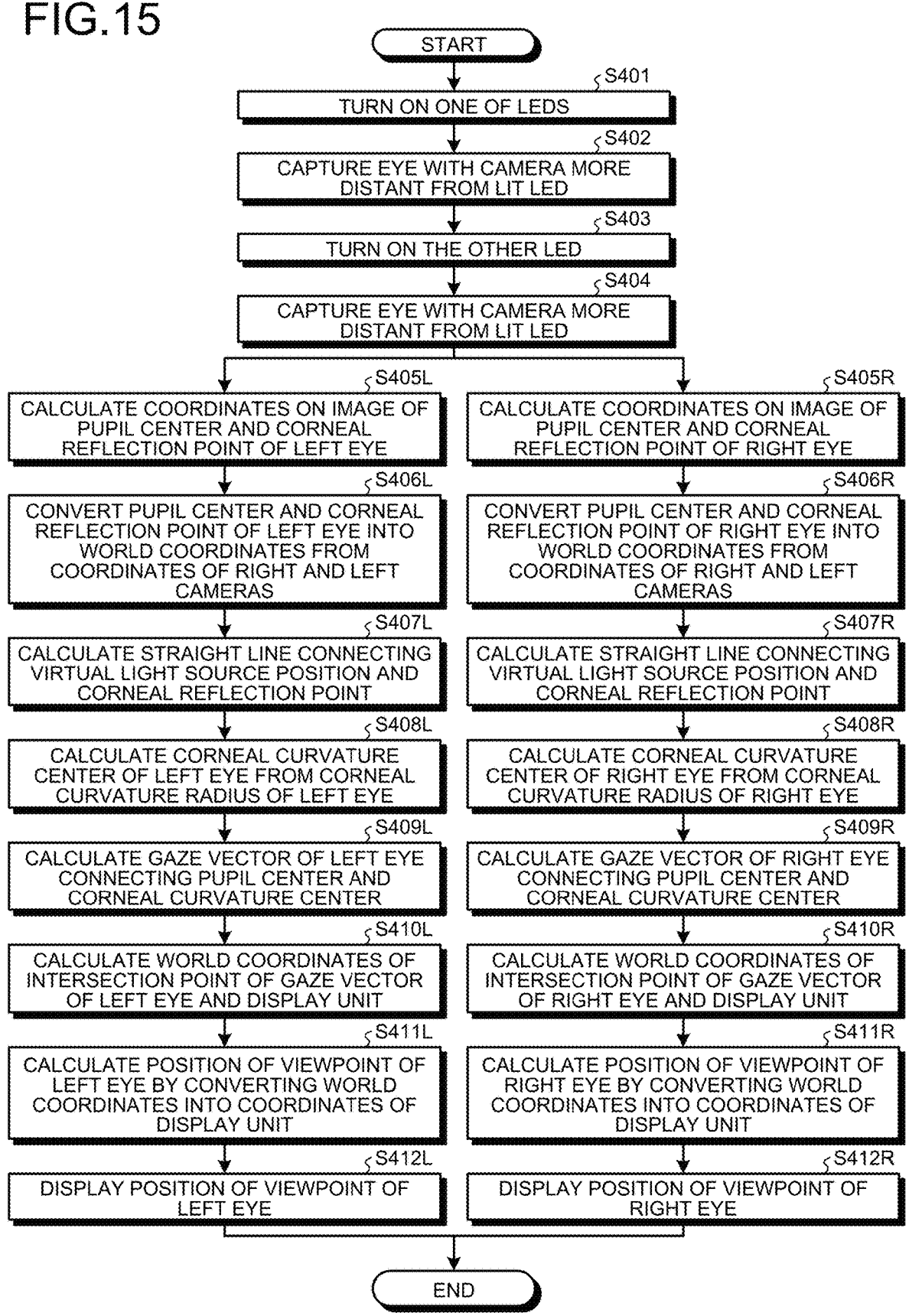
FIG. 15 is a flowchart illustrating an example of the gaze detection processing of the present embodiment.

FIG. 14 is a flowchart illustrating an example of calibration processing when the corneal curvature radii of the right and left eyeballs are individually stored in the storage unit 150. FIG. 15 is a flowchart illustrating an example of gaze detection processing when the viewpoints of the right and left eyeballs are individually displayed on the display unit 101.

First, the calibration processing according to the present embodiment will be described with reference to FIG. 14. Processing from Step S301 to Step S305 is similar to the processing from Step S101 to Step S105 described with reference to FIG. 10, and thus the description is omitted. Processing from Step S306L to Step S312L for the left eye is similar to the processing from Step S106L to Step S112L described with reference to FIG. 10, and thus description is omitted. Processing from Step S306R to Step S312R for the right eye is similar to the processing from Step S106R to Step S112R described with reference to FIG. 10, and thus description is omitted.

The curvature radius calculation unit 353 calculates the corneal curvature radius r1 of the left eye of the subject (Step S312L) and stores the calculated corneal curvature radius r1 of the left eye in the storage unit 150 (Step S313L). Further, the curvature radius calculation unit 353 calculates the corneal curvature radius r2 of the right eye of the subject (Step S312R), and stores the calculated corneal curvature radius r2 of the right eye in the storage unit 150 (Step S313R).

Next, gaze detection processing according to the present embodiment will be described with reference to FIG. 15. Processing from Step S401 to Step S404 is similar to the processing from Step S201 to Step S204 described with reference to FIG. 12, and thus the description is omitted. Processing from Step S405L to Step S407L for the left eye is similar to the processing from Step S205L to Step S207L described with reference to FIG. 12, and thus the description is omitted. Processing from Step S405R to Step S407R for the right eye is similar to the processing from Step S205R to Step S207R described with reference to FIG. 12, and thus the description is omitted.

The gaze detection unit 354 calculates the world coordinate values of the pupil center and the corneal reflection center of the left eye of the subject, and calculates the corneal curvature center of the left eye of the subject on the basis of the corneal curvature radius r1 stored in the storage unit 150 in Step S313L in FIG. 14 (Step S408L).

The gaze detection unit 354 obtains a gaze vector connecting the pupil center and the corneal curvature center of the left eye (Step S409L). The viewpoint detection unit 355 calculates a three-dimensional world coordinate value of an intersection point between the gaze vector of the left eye and the screen of the display unit 101 (Step S410L). The viewpoint detection unit 355 converts the obtained three-dimensional world coordinate value into coordinate values (x1, y1) expressed by the two-dimensional coordinate system of the display unit 101. With the conversion, the position of the viewpoint on the display unit 101 that the left eye of the subject is gazing at, is calculated (Step S411L). The output control unit 356 displays the coordinate values (x1, y1) of the viewpoint of the left eye calculated in Step S411L on the display unit 101 (Step S412L).

Further, the gaze detection unit 354 calculates the world coordinate values of the pupil center and the corneal reflection center of the right eye of the subject, and calculates the corneal curvature center of the right eye of the subject on the basis of the corneal curvature radius r2 stored in the storage unit 150 in Step S313R in FIG. 14 (Step S408R).

The gaze detection unit 354 obtains a gaze vector connecting the pupil center and the corneal curvature center of the right eye (Step S409R). The viewpoint detection unit 355 calculates a three-dimensional world coordinate value of an intersection point between the gaze vector of the right eye and the screen of the display unit 101 (Step S410R). The viewpoint detection unit 355 converts the obtained three-dimensional world coordinate value into coordinate values (x2, y2) expressed by the two-dimensional coordinate system of the display unit 101. With the conversion, the position of the viewpoint on the display unit 101 that the right eye of the subject is gazing at, is calculated (Step S411R). The output control unit 356 displays the coordinate values (x2, y2) of the viewpoint of the right eye calculated in Step S411R on the display unit 101 (Step S412R).

Figure 16:
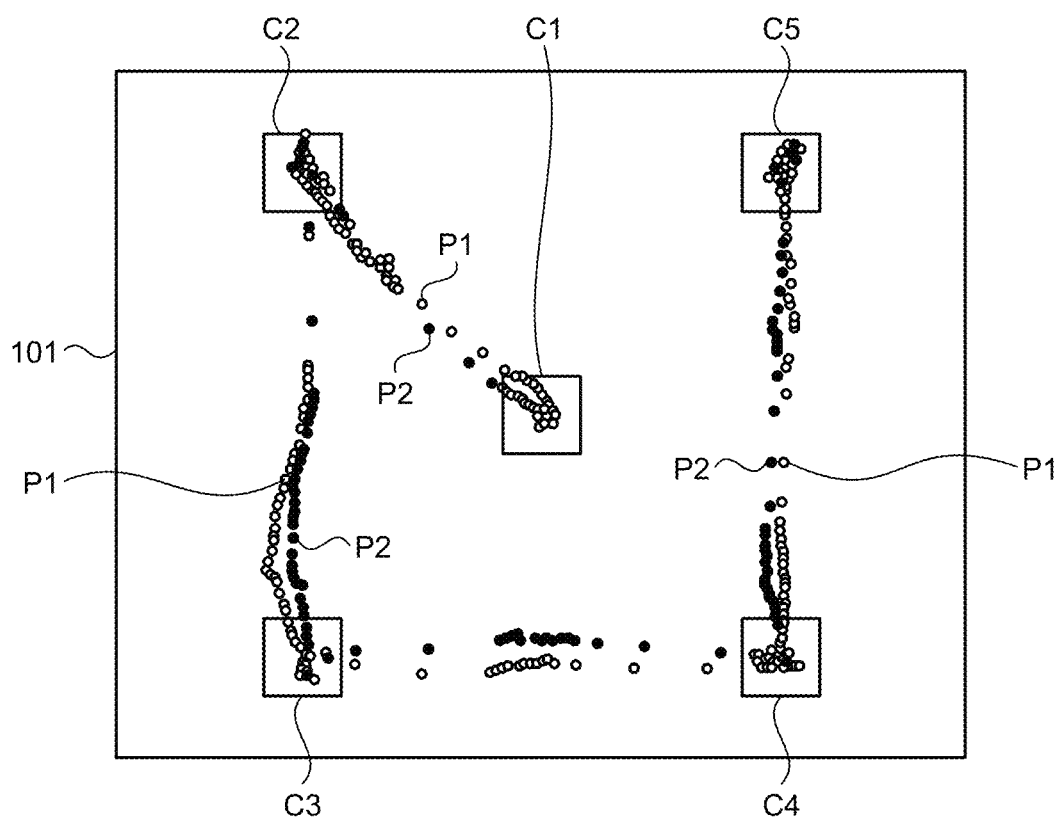
FIG. 16 is a diagram illustrating a display example of the display unit of the present embodiment.

FIG. 16 is a diagram illustrating an example of viewpoints displayed on the display unit 101 by the output control unit 356 in Steps S412L and S412R. Index images C1, C2, C3, C4, and C5 are displayed on the display unit 101. To evaluate how the eyeballs of the subject move, the subject is instructed to move the viewpoints of both the right and left eyeballs in order of the index images C1, C2, C3, C4, and C5.

After the detection of the viewpoints is performed, the operation input unit provided in the diagnosis support apparatus 100 is operated by the operator or the subject, and a plot point P1 indicating the viewpoint of the left eye and a plot point P2 indicating the viewpoint of the right eye are individually displayed on the display unit 101 by the operation.

As illustrated in FIG. 16, the output control unit 356 displays the plot points P1 and P2 indicating the viewpoints of the right and left respective eyeballs on the display unit 101 in different modes. The mode of the plot points P1 and P2 displayed on the display unit 101 includes at least one of color, shape, and size. For example, the plot point P1 may be displayed in "blue" and the plot point P2 may be displayed in "gray", the plot point P1 may be displayed by "o" and the plot point P2 may be displayed by "x", or the plot point P1 may be displayed by large "o" and the plot point P2 may be displayed by small "o".

Figure 17:
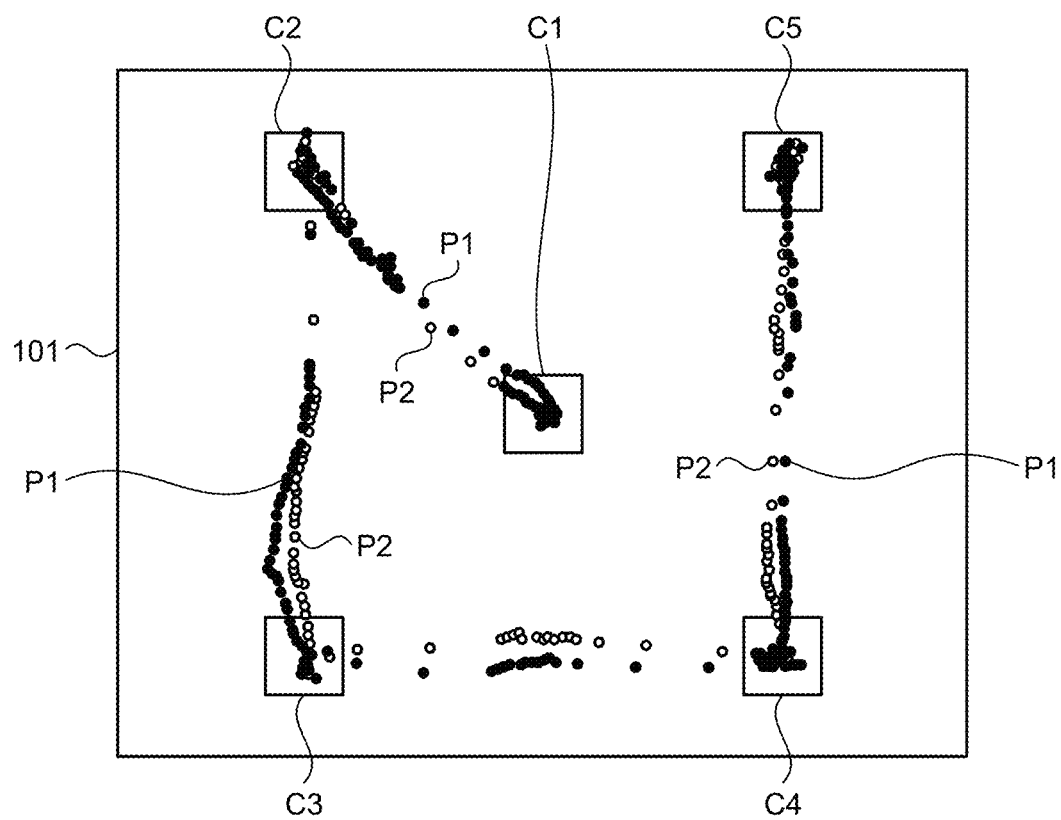
FIG. 17 is a diagram illustrating a display example of the display unit of the present embodiment.

Further, as illustrated in FIG. 17, the output control unit 356 can switch the display mode between the plot point P1 indicating the viewpoint of the left eye and the plot point P2 indicating the view point of the right eye. For example, in the example illustrated in FIG. 16, in the case where the plot point P1 is displayed in "blue" and the plot point P2 is displayed in "gray", the output control unit 356 can display the plot point P1 in "gray" and the plot point P2 in "blue", as illustrated in FIG. 17. Similarly, the output control unit 356 can switch the state in which the plot point P1 is displayed by "o" and the plot point P2 is displayed by "x" into the state in which the plot point P1 is displayed by "x" and the plot point P2 is displayed by "o".

By displaying the viewpoints of the right and left respective eyeballs on the display unit 101 in different modes, the operator or the subject can easily know which plot point represents the viewpoint of the left eye or the viewpoint of the right eye.

Figure 18:
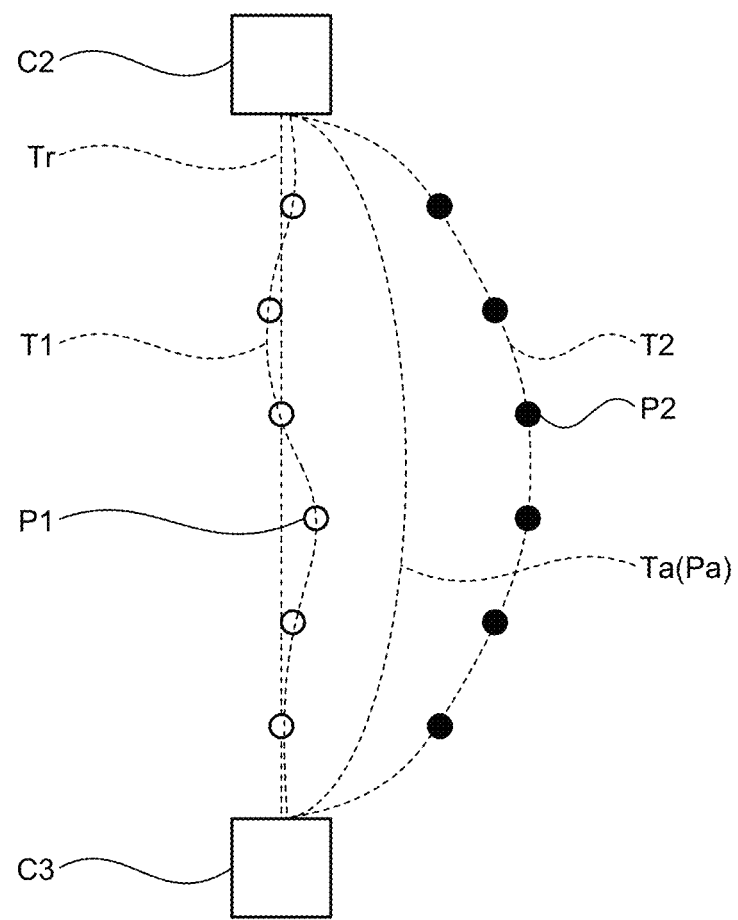
FIG. 18 is a diagram illustrating a display example of the display unit of the present embodiment.

FIG. 18 is an enlarged view of a part of the display unit 101 according to the present embodiment. For example, in a subject having substantially different gaze directions of the right and left eyeballs due to an influence of strabismus or the like, a first movement locus T1 of the plot point P1 indicating the viewpoint of the left eye and a second movement locus T2 of the plot point P2 indicating the viewpoint of the right eye may be substantially different, as illustrated in FIG. 18. As illustrated in FIG. 18, in the case where the subject is instructed to move the viewpoint from the index image C2 to the index image C3, for example, and the right eye has strabismus, the first movement locus T1 of the plot point P1 indicating the gaze point of the left eye without strabismus moves along a linear target locus Tr connecting the index image C2 and the index image C3, whereas the second movement locus T2 of the plot point P2 indicating the gaze point of the right eye with strabismus may significantly deviate from the target locus Tr. If an averaged gaze point Pa of the gaze points of the right and left eyeballs is calculated for the subject having substantially different first movement locus T1 and second movement locus T2, a movement locus Ta of the averaged gaze point Pa deviates from the correct first movement locus T1, and detection of a correct gaze direction or viewpoint becomes difficult.

Further, for example, when the right eye has strabismus and when an object A is displayed on the right side and an object B is displayed on the left side of the display screen, the viewpoint of the left eye exists on the left side with respect to the object A on the display screen when the viewpoint of the right eye exists near the object A. Similarly, when the viewpoint of the left eye is near the object B, the viewpoint of the right eye exists on the right side with respect to the object B on the display screen. If the positions of the viewpoints are averaged, the averaged viewpoint does not exist on the objects A and B, accurate diagnosis cannot be performed.

According to the present embodiment, the corneal curvature radii of the right and left respective eyeballs are stored in the storage unit 150, and the gaze directions or the positions of the viewpoints are individually displayed on the display unit 101. Therefore, accurate diagnosis can be performed.

Figure 19:
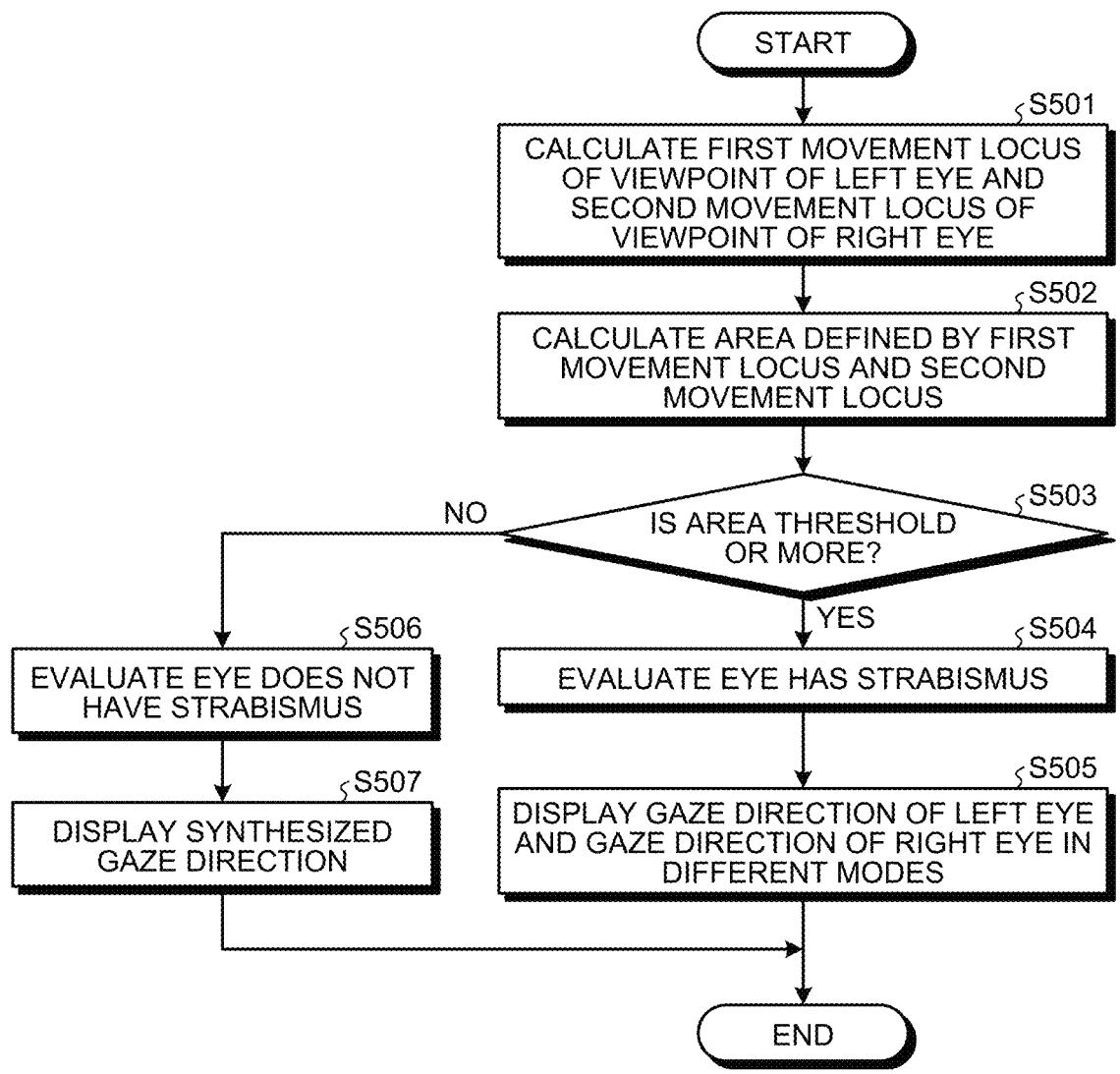
FIG. 19 is a flowchart illustrating an example of an evaluation method of the present embodiment.
Figure 20:
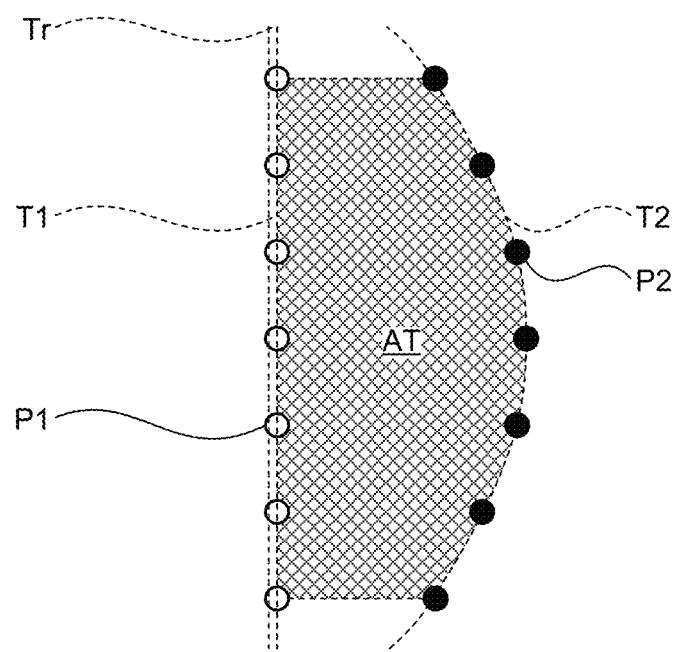
FIG. 20 is a schematic diagram for describing an example of the evaluation method of the present embodiment.

Next, an evaluation method of respective states of the right and left eyeballs according to the present embodiment will be described. FIG. 19 is a flowchart illustrating an example of the evaluation method according to the present embodiment. FIG. 20 is a schematic diagram for describing an example of the evaluation method of the present embodiment.

The viewpoint detection unit 355 calculates the first movement locus T1 of the plot point P1 indicating the viewpoint of the left eye and the second movement locus T2 of the plot point P2 indicating the viewpoint of the right eye (Step S501). The viewpoint detection unit 355 extracts a plurality of the plot points P1 in a predetermined period or in a moving distance of the viewpoints, performs fitting processing of the plurality of plot points P1, and calculates the first movement locus T1. Similarly, the viewpoint detection unit 355 performs fitting processing of a plurality of extracted plot points P2, and calculates the second movement locus T2.

For example, as illustrated in FIG. 20, in the case where seven plot points P1 are extracted and seven plot points P2 are extracted in a predetermined period or in a moving distance of the viewpoints, the viewpoint detection unit 355 performs fitting processing of the seven plot points P1 to obtain a curve indicating the first movement locus T1, and performs fitting processing of the seven plot points P2 to obtain a curve indicating the second movement locus T2.

The viewpoint detection unit 355 calculates an area AT defined by the first movement locus T1 and the second movement locus T2 (Step S502). Specifically, the viewpoint detection unit 355 calculates the area AT of a region surrounded by a straight line connecting the plot point P1 and the plot point P2 closest to a starting point of the predetermined period or the moving distance, a straight line connecting the plot point P1 and the plot point P2 closest to an end point of the predetermined period or the moving distance, the curve indicating the first movement locus T1 and the curve indicating the second movement locus T2.

The determination unit 358 determines whether the area AT calculated in Step S502 is equal to or larger than a predetermined threshold (Step S503).

In Step S503, when the area AT is determined to be equal to or larger than the threshold (Step S503: Yes), the determination unit 358 determines that at least one of the right and left eyeballs does not face the target direction.

The evaluation unit 357 evaluates respective states of the right and left eyeballs from movement loci T1 and T2 of the viewpoints of the right and left respective eyeballs. The evaluation unit 357 compares the first movement locus T1, the second movement locus T2, and the target movement locus Tr. When a deviation amount (shift amount) of the first movement locus T1 from the target movement locus Tr is small, a deviation amount of the second movement locus T2 from the target movement locus Tr is large, and the area AT is equal to or larger than the threshold, the evaluation unit 357 evaluates that the state of the right eye is in some abnormal state such as strabismus (Step S504).

When the determination unit 358 determines that one of the right and left eyeballs does not face the target direction, the output control unit 356 individually displays the plot point P1 indicating the viewpoint of the left eye and the plot point P2 indicating the viewpoint of the right eye on the display unit 101.

In the present embodiment, when the determination unit 358 determines that one of the right and left eyeballs does not face the target direction, the output control unit 356 displays the gaze direction or the viewpoint of the eyeball that is determined not to face the target direction, and the gaze direction or the viewpoint of the eyeball that is determined to face the target direction on the display unit 101 in different modes (Step S505). For example, in the case where the left eye is determined to face the target direction and the right eye is determined not to face the target direction (strabismus), the output control unit 356 can emphasize and display the plot point P1 by displaying the plot point P1 with high brightness, by displaying the plot point P1 in a large manner, or by continuously lighting the plot point P1, and can display the plot point P2 by displaying the plot point P2 with low brightness, by displaying the plot point P2 in a small manner, or by blinking the plot point P2. Further, the output control unit 356 may display the plot point P1 and not display the plot point P2.

In Step S503, when the area AT is determined to be smaller than the threshold (Step S503: No), the determination unit 358 determines that both the right and left eyeballs face the target direction. That is, the determination unit 358 determines that the gaze direction of the left eye and the gaze direction of the right eye accord.

The evaluation unit 357 compares the first movement locus T1, the second movement locus T2, and the target movement locus Tr. When the deviation amount of the first movement locus T1 from the target movement locus Tr and the deviation amount of the second movement locus T2 from the target movement locus Tr are small, and the area AT is smaller than the threshold, the evaluation unit 357 evaluates that the subject does not have strabismus, and the right and left respective eyeballs are in a normal state (Step S506).

When the determination unit 358 determines that both the right and left eyeballs face the target direction, the output control unit 356 displays a synthesized gaze direction in which the gaze direction of the left eyeball and the gaze direction of the left eyeball are synthesized on the display unit 101 (Step S507). That is, in the present embodiment, when the subject is determined not to have strabismus, the output control unit 356 averages the position of the viewpoint of the right eyeball and the position of the viewpoint of the left eyeball, as described with reference to FIG. 13 and the like, and displays a synthesized gaze direction in which the gaze direction of the right eyeball and the gaze direction of the left eyeball are synthesized on the display unit 101, rather than individually displaying the viewpoint of the left eye and the viewpoint of the right eye.

Note that, when the determination unit 358 determines that both the right and left eyeballs face the target direction, the output control unit 356 may individually display the gaze direction or the viewpoint of the left eyeball, and the gaze direction or the viewpoint of the right eyeball on the display unit 101.

As described above, according to the present embodiment, the corneal curvature radii of the right and left respective eyeballs are calculated and individually stored in the storage unit 150, and the gaze directions of the right and left respective eyeballs are detected and individually displayed on the display unit 101. With the configuration, the gaze direction can be accurately detected for both the subject having substantially different gaze directions of the right and left eyeballs and the subject having substantially equal gaze directions of the right and left eyeballs.

Further, according to the present embodiment, both the gaze direction or the viewpoint of the left eye and the viewpoint direction or the viewpoint of the right eye are displayed on the display unit 101. Therefore, the operator or the subject can grasp the state of the left eye and the state of the right eye by viewing the display unit 101.

Further, in the present embodiment, the viewpoint of the left eye and the viewpoint of the right eye are displayed on the display unit 101 in different modes. Therefore, the operator or the subject can easily distinguish the viewpoint of the left eye and the viewpoint of the right eye by viewing the display unit 101.

Further, in the present embodiment, the first movement locus T1 of the viewpoint of the left eye and the second movement locus T2 of the viewpoint of the right eye are respectively calculated. Therefore, the state of the left eye and the state of the right eye can be individually evaluated.

Further, in the present embodiment, the gaze direction of the left eye and the gaze direction of the right eye are separately detected. Therefore, whether the right and left eyeballs face the target direction can be determined. When one of the right and left eyeballs is determined not to face the target direction, the gaze direction of the eyeball that is determined not to face the target direction, and the gaze direction of the eyeball that is determined to face the target direction are displayed on the display unit 101 in different modes. With the operation, the operator or the subject can easily grasp which one of the left eye and the right eye does not face the target direction by viewing the display unit 101. Further, by highlighting the viewpoint of the eye determined to face the target direction or by not displaying the viewpoint of the eye determined not to face the target direction, the operator or the subject can smoothly grasp the viewpoint of the eye in the normal state by viewing the display unit 101.

Further, in the present embodiment, when both the right and left eyeballs are determined to face the target direction, the synthesized gaze direction in which the gaze direction of the right eyeball and the gaze direction of the left eyeball are synthesized (averaged viewpoint) is displayed on the display unit 101. With the configuration, the operator or the subject can grasp the movement of the gaze of the subject who does not have strabismus.

Further, in the present embodiment, whether the right and left eyeballs face the target direction can be accurately determined on the basis of the first movement locus T1 of the viewpoint of the left eye, the second movement locus T2 of the viewpoint of the right eye, and the area AT defined by the first movement locus T1 and the second movement locus T2.

Figure 21:
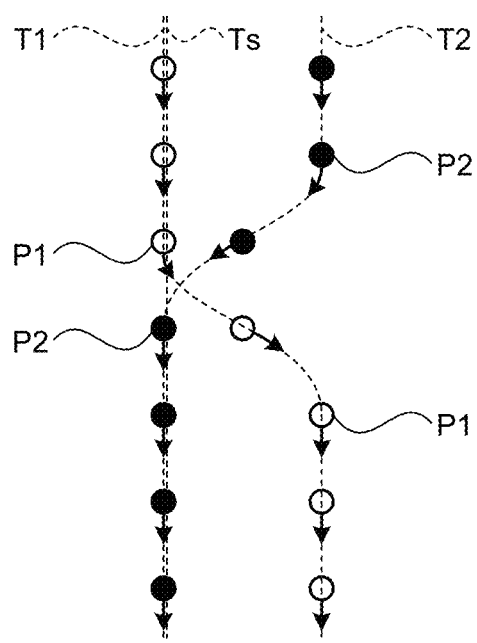
FIG. 21 is a schematic diagram for describing an example of the evaluation method of the present embodiment.

Note that, in the present embodiment, an example of evaluating whether the subject has strabismus has been mainly described. Even when the subject does not have strabismus, the evaluation unit 357 can evaluate the respective states of the right and left eyeballs from the movement loci of the viewpoints of the right and left respective eyeballs. For example, as illustrated in FIG. 21, the evaluation unit 357 can evaluate how the left eye moves on the basis of a vector from the plot point P1 to an adjacent plot point P1, and can evaluate how the right eye moves on the basis of a vector from the plot point P2 to an adjacent plot point P2. Since both the plot point P1 and the plot point P2 are displayed, the way of movement of the left eye and the way of movement of the right eye can be separately evaluated. Further, there may be a case in which at least one of the movement of the viewpoint of the left eye and the movement of the viewpoint of the right eye blurs, and as illustrated in FIG. 21, the first movement locus T1 and the second movement locus T2 intersect. Further, there is a possibility that the numbers of acquired plot points may differ between the left eye and the right eye in a predetermined period or in a moving distance of the gaze due to a difference in length or timing of blinks between the right and left eyes. In that case, the viewpoint of the subject may be evaluated as moving along a straight line Ts including a part of the first movement locus T1 and a part of the second movement locus T2.

Modification

The calibration processing of calculating the distance between the pupil center position and the corneal curvature center position is not limited to the method described with reference to FIGS. 9 and 10. Hereinafter, another example of the calculation processing will be described with reference to FIGS. 22 and 23.

Figure 22:
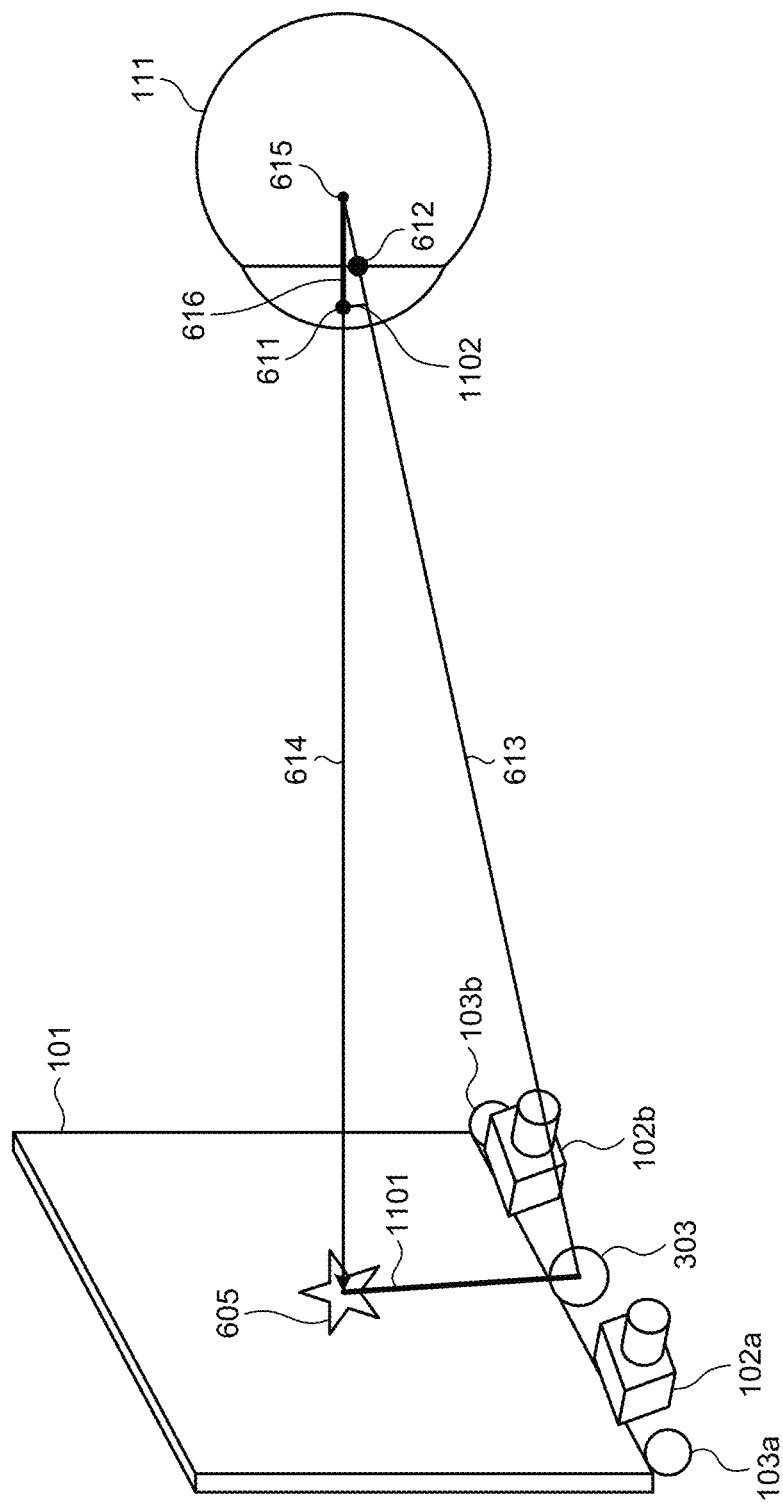
FIG. 22 is a diagram for describing calculation processing of a modification.

FIG. 22 is a diagram for describing calculation processing of the present modification. The same reference numerals are given to elements that have been described in FIGS. 3 to 6, and 9, and description of the elements is omitted.

A line segment 1101 is a line segment (first line segment) connecting a target position 605 and a virtual light source position. A line segment 1102 is a line segment (second line segment) that is parallel to the line segment 1101 and connects a pupil center 611 and a straight line 613. In the present modification, a distance 616 between the pupil center 611 and a corneal curvature center 615 is calculated and stored using the line segment 1101 and the line segment 1102, as described below.

Figure 23:
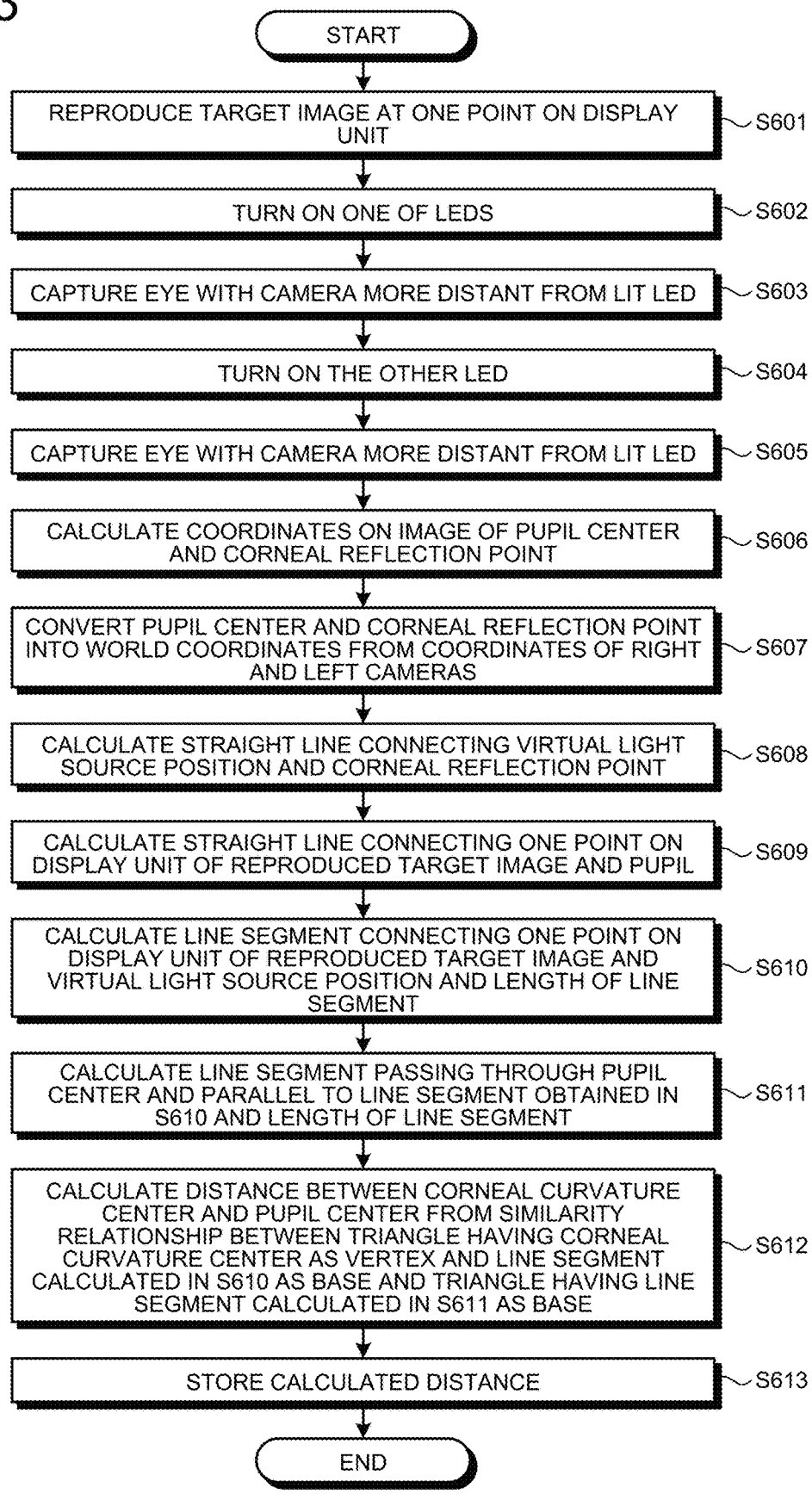
FIG. 23 is a flowchart illustrating an example of the calculation processing of a modification.

FIG. 23 is a flowchart illustrating an example of calculation processing of the present modification. Note that FIG. 23 illustrates processing for one of right and left eyeballs. Steps S601 to S609 are similar to Steps S101 to S109 in FIG. 10, and thus description is omitted.

A curvature radius calculation unit 353 calculates a line segment (line segment 1101 in FIG. 22) connecting a center of a target image displayed at one point on a screen of a display unit 101 and the virtual light source position, and calculates a length (L1101) of the calculated line segment (Step S610).

The curvature radius calculation unit 353 calculates a line segment (line segment 1102 in FIG. 22) passing through the pupil center 611, parallel to the line segment calculated in Step S610, and calculates a length (L1102) of the calculated line segment (Step S611).

The curvature radius calculation unit 353 calculates the distance 616 between the pupil center 611 and the corneal curvature center 615 on the basis of the fact that a triangle having the corneal curvature center 615 as a vertex and having the line segment calculated in Step S610 as a base, and a triangle having the corneal curvature center 615 as a vertex and having the line segment calculated in Step S611 as a base are in a similarity relationship (Step S612). For example, the curvature radius calculation unit 353 calculates the distance 616 such that a ratio of the length of the line segment 1102 to the length of the line segment 1101 and a ratio of the distance 616 to the distance between the target position 605 and the corneal curvature center 615 become equal.

The distance 616 can be calculated by the following expression (1). Note that L614 is a distance from the target position 605 to the pupil center 611.

$$\text{The distance } 616 = (L614 \times L1102)/(L1101 - L1102). \quad (1)$$

The curvature radius calculation unit 353 stores the calculated distance 616 in the storage unit 150 or the like (Step S613). The stored distance is used to calculate the corneal curvature center at the time of subsequent viewpoint (gaze) detection.

REFERENCE SIGNS LIST

The gaze detection apparatus and the gaze detection method according to the present disclosure exhibit an effect to accurately detect gaze directions of various subjects.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A gaze detection apparatus comprising:
   a processor that executes computer-executable components, the computer-executable components comprising:
   a display unit configured to display index images;
   a light source configured to irradiate an eyeball of a subject with detection light;
   a position detection unit configured to detect positions of pupil centers indicating centers of pupils of respective right and left eyeballs and positions of corneal reflection centers indicating respective centers of corneal reflexes of the right and left eyeballs from an image of the eyeball irradiated with the detection light;
   a curvature radius calculation unit configured to calculate respective corneal curvature radii of the right and left eyeballs from a position of the light source and the positions of the corneal reflection centers;
   a gaze detection unit configured to detect respective gaze directions of the right and left eyeballs from the positions of the pupil centers and the corneal curvature radii;
   a viewpoint detection unit configured to detect respective viewpoints of the right and left eyeballs from the gaze directions detected by the gaze detection unit; and
   an output control unit configured to display the respective viewpoints of the right and left eyeballs on the display unit on which the index images are displayed from the gaze directions detected by the gaze detection unit.

2. The gaze detection apparatus according to claim 1, wherein the output control unit displays the respective viewpoints of the right and left eyeballs on the display unit in different display modes, and wherein the different display modes differ in terms of at least one of luminance, color, shape, or size.

3. The gaze detection apparatus according to claim 1, wherein the computer-executable components further comprise:
   an evaluation unit configured to evaluate respective states of right and left eyeballs from movement loci of respective viewpoints of right and left eyeballs.

4. The gaze detection apparatus according to claim 1, wherein the display unit is configured to move the index images within a display area.

5. The gaze detection apparatus according to claim 1, wherein the computer-executable components further comprise:
   a determination unit configured to determine whether the right and left eyeballs face a target direction based on the gaze directions detected by the gaze detection unit, wherein the determination unit determines whether both the right and left eyeballs face the target direction based on a first movement locus of the viewpoint of the left eyeball, a second movement locus of the viewpoint of the right eyeball, and an area defined by the first movement locus and the second movement locus.

6. The gaze detection apparatus according to claim 5, wherein,
   in response to a determination by the determination unit that one of the right eyeball or the left eyeball is not facing the target direction,
   the output control unit displays the gaze direction of the eyeball, of the right eyeball or the left eyeball, that is not facing the target direction, and the gaze direction of the other eyeball, of the right eyeball or the left eyeball, that is facing the target direction, on the display unit in different display modes, and
   different display modes differ in terms of at least one of luminance, color, shape, or size.

7. The gaze detection apparatus according to claim 5, wherein,
   in response to a determination by the determination unit that both the right and left eyeballs are facing the target direction, the output control unit displays, on the display unit, a synthesized gaze direction in which the gaze direction of the right eyeball and the gaze direction of the left eyeball are synthesized.

8. A gaze detection method, comprising:
   displaying an index images on a display unit;

irradiating an eyeball of a subject with detection light emitted from a light source;

detecting positions of pupil centers indicating centers of pupils of respective right and left eyeballs and respective positions of corneal reflection centers indicating centers of corneal reflexes of the right and left eyeballs based on an image of the eyeball irradiated with the detection light;

calculating respective corneal curvature radii of the right and left eyeballs based on a position of the light source and the positions of the corneal reflection centers;

detecting respective gaze directions of the right and left eyeballs based on the positions of the pupil centers and the corneal curvature radii;

detecting respective viewpoints of the right and left eyeballs based on the detected gaze directions; and displaying the respective viewpoints of the right and left eyeballs on the display unit on which the index images are displayed based on the detected gaze directions.

* * * * *